United States Patent
Hosoe

(10) Patent No.: US 12,391,922 B2
(45) Date of Patent: Aug. 19, 2025

(54) PLATELET LYSATE PRODUCTION METHOD, PRODUCTION SYSTEM, AND BAG SET

(71) Applicant: TERUMO KABUSHIKI KAISHA, Tokyo (JP)

(72) Inventor: Kaoru Hosoe, Shizuoka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 820 days.

(21) Appl. No.: 17/428,561

(22) PCT Filed: Feb. 14, 2020

(86) PCT No.: PCT/JP2020/005785
§ 371 (c)(1),
(2) Date: Aug. 4, 2021

(87) PCT Pub. No.: WO2020/166700
PCT Pub. Date: Aug. 20, 2020

(65) Prior Publication Data
US 2022/0127573 A1  Apr. 28, 2022

(30) Foreign Application Priority Data
Feb. 15, 2019 (JP) .................. 2019-025982

(51) Int. Cl.
*B01D 21/26* (2006.01)
*A61J 1/12* (2006.01)
(Continued)

(52) U.S. Cl.
CPC .............. *C12N 5/0644* (2013.01); *A61J 1/12* (2013.01); *A61M 1/0272* (2013.01); *B01D 21/262* (2013.01)

(58) Field of Classification Search
CPC .................................................. A61M 1/0272
See application file for complete search history.

(56) References Cited

U.S. PATENT DOCUMENTS 3,064,647 A * 11/1962 Earl ........................... A61J 1/10
 494/21
3,986,506 A * 10/1976 Garber .................. A61M 1/369
 604/262

(Continued)

FOREIGN PATENT DOCUMENTS

| | | | |
|---|---|---|---|
| CN | 206980183 U | * | 2/2018 |
| JP | S63-3867 | | 1/1988 |

(Continued)

OTHER PUBLICATIONS

English translation of WO 2012/144312. (Year: 2012).*
(Continued)

*Primary Examiner* — Leslie R Deak
(74) *Attorney, Agent, or Firm* — Sheridan Ross P.C.

(57) ABSTRACT

Provided are a method for producing a platelet lysate, a production system, and a bag set capable of efficiently producing a platelet lysate with a simple device structure. According to the method for producing a platelet lysate, by which a platelet lysate (PL) that contains a growth factor contained in platelet is produced, buffy coat is collected from whole blood; the buffy coat (BC) is centrifuged to extract a supernatant, thereby collecting a platelet concentrate from which leukocyte has been removed; and, prior to freezing, the platelet concentrate is centrifuged to remove the supernatant, thereby preparing a highly concentrated platelet concentrate. The highly concentrated platelet concentrate is then frozen and thawed, and further centrifuged to recover the platelet lysate.

3 Claims, 22 Drawing Sheets

(51) Int. Cl.
   *A61M 1/02* (2006.01)
   *C12N 5/078* (2010.01)

(56) References Cited

U.S. PATENT DOCUMENTS

| | | | |
|---|---|---|---|
| 4,197,847 A * | 4/1980 | Djerassi | A61M 1/3616 604/6.02 |
| 4,663,032 A | 5/1987 | Loos et al. | |
| 4,994,039 A * | 2/1991 | Mattson | A61M 1/0209 604/408 |
| 2002/0192632 A1 | 12/2002 | Hei et al. | |
| 2004/0009542 A1 | 1/2004 | Dumont et al. | |
| 2005/0256443 A1 | 11/2005 | Bischof et al. | |
| 2006/0180526 A1 | 8/2006 | Sugawara et al. | |
| 2011/0033554 A1 | 2/2011 | Burnouf et al. | |
| 2012/0276632 A1 | 11/2012 | Strunk et al. | |
| 2012/0289926 A1 | 11/2012 | Hirabuki et al. | |
| 2014/0301914 A1 | 10/2014 | Suzuki et al. | |
| 2017/0202882 A1 | 7/2017 | Vermeij | |

FOREIGN PATENT DOCUMENTS

| | | |
|---|---|---|
| JP | H04-236959 | 8/1992 |
| JP | 2007-265407 A | 10/1995 |
| JP | H11-056351 | 3/1999 |
| JP | 2000-334034 A | 12/2000 |
| JP | 2002-541941 | 12/2002 |
| JP | 2003-052814 | 2/2003 |
| JP | 2004-073602 | 3/2004 |
| JP | 2005-000394 | 1/2005 |
| JP | 2005-511197 | 4/2005 |
| JP | 2005-524445 | 8/2005 |
| JP | 2008-086235 | 4/2008 |
| JP | 2010-227582 | 10/2010 |
| JP | 2011-515170 | 5/2011 |
| JP | 2012-067126 | 4/2012 |
| JP | 6000974 | 10/2016 |
| WO | WO 00/62891 | 10/2000 |
| WO | WO 2004/082741 | 9/2004 |
| WO | WO 2005/032565 | 4/2005 |
| WO | WO 2005/032618 | 4/2005 |
| WO | WO 2011/058868 | 5/2011 |
| WO | WO 2012/144312 | 10/2012 |
| WO | 2013042095 A1 | 3/2013 |
| WO | WO 2015/088019 | 6/2015 |
| WO | WO 2017/211906 | 12/2017 |
| WO | WO 2018/162740 | 9/2018 |

OTHER PUBLICATIONS

Extended European Search Report for Europe Patent Application No. 20756463.4, dated Apr. 6, 2023, 21 pages.
International Searching Authority, International Search Report, PCT/JP2020/005785; Apr. 10, 2020, 5 pages.
Senku et al., "SY3-2. Examination of a preparation method and the evaluation of the platelet dissolution liquid to add in the amplification of cells used in regenerative therapy, cell therapy (Platelet lysate)," Journal of the Society for Japanese Blood Programme, vol. 41, No. 2, 2018, p. 408 (with English machine translation).
Meyer et al., "Filter Buffy Coats (Fbc): A source of peripheral blood leukocytes recovered from leukocytes depletion filters," Journal of Immunological Methods, vol. 307, Nov. 17, 2005, pp. 150-166.
Nakajo et al., "Comparison of a "Top and Bottom" System with a Conventional Quadruple-Bag System for Blood Component Preparation and Storage," Japanese Journal of Transfusion Medicine, vol. 38, No. 3, 1992, pp. 392-400 (with English translation).
Third Party Submission (English machine translation only) for Japan Patent Application No. 2020-572335, dated Mar. 23, 2024, 2 pages.
Official Action (with English translation) for Japan Patent Application No. 2020-572335, dated Sep. 19, 2023, 14 pages.
English Translation of Official Action for Japan Patent Application No. JP 2024-084244, dated Jun. 10, 2025, 5 pages.
English Translation of Official Action for Japan Patent Application No. JP 2024-084243, dated Jun. 10, 2025, 10 pages.

* cited by examiner

PLATELET LYSATE PRODUCTION METHOD, PRODUCTION SYSTEM, AND BAG SET

TECHNICAL FIELD

The present invention relates to a method for producing platelet lysate for extracting a growth factor contained in platelet, a production system, and a bag set.

BACKGROUND ART

In recent years, there has been advancing clinical application of cell therapy, in which a cell collected from biological tissue is cultured in vitro, amplified up to a required population, and put into therapy. Among others, mesenchymal stem cell is expected to be applied to regenerative medicine such as reconstruction of bone, blood vessel and myocardium, for its potential to differentiation into various cells. For wide spreading of such cell therapy, a cell culture medium capable of efficiently culturing an intended cell is desired.

It has been a general consensus that the cell culture medium for mesenchymal stem cell essentially contains an animal-derived growth factor such as fetal bovine serum (FBS). Recent proposal, however, relates to a growth factor extracted from platelet contained in human blood, as an alternative to the animal-derived growth factor such as FBS ("Human platelet lysate: Replacing fetal bovine serum as a gold standard for human cell propagation?", Thierry Burnouf, et al., Biomaterials, Vol. 76, January 2016, Pages 371-387). This growth factor is obtained by extracting a growth factor contained in intracellular granule of platelet to the outside of the cell, and is also referred to as platelet lysate (PL) since it is obtainable by lysing platelet. Some reports describe that the platelet lysate has a higher ability to culture mesenchymal stem cell, than FBS.

According to a known method for preparing the platelet lysate, platelet separated from whole blood (WB) is frozen and thawed to break the cell membrane, thereby extracellularly extracting the growth factor in the granule.

SUMMARY OF INVENTION

The present invention is conceived regarding production of the platelet lysate, wherein an object thereof is to provide a method for producing a platelet lysate, a production system and a bag set, capable of efficiently producing a platelet lysate with a simple device structure.

According to one aspect of the present invention, there is provided a method for producing a platelet lysate, the method includes: collecting from a donor a platelet concentrate that contains platelet; freezing and thawing the platelet concentrate; and centrifuging, following freezing and thawing, the platelet concentrate to recover a platelet lysate.

According to another aspect of the present invention, there is provided a method for producing a platelet lysate, the method includes: collecting a buffy coat from whole blood; centrifuging the buffy coat to extract a supernatant, and removing leukocyte to collect a platelet concentrate; centrifuging, prior to freezing, the platelet concentrate, and removing a supernatant to further densify platelet in the platelet concentrate, to prepare a highly concentrated platelet concentrate; freezing and thawing the highly concentrated platelet concentrate; and centrifuging the highly concentrated platelet concentrate, having been frozen and thawed, to separate a supernatant, and recovering it as the platelet lysate.

According to another aspect of the present invention, there is provided a method for producing a platelet lysate, the method includes: collecting whole blood from a donor; allowing the collected whole blood to pass through a leukapheresis filter to remove leukocyte; flushing a platelet recovery liquid through the leukapheresis filter through which the whole blood has been allowed to pass, in a direction opposite to a flow direction of the whole blood, to recover platelet retained on the leukapheresis filter as a platelet-containing liquid; further centrifuging the platelet-containing liquid to remove a supernatant, and thus concentrating platelet to prepare a platelet concentrate; freezing and thawing the platelet concentrate; and centrifuging the platelet concentrate, following freezing and thawing, to recover a supernatant as the platelet lysate.

According to another aspect of the present invention, there is provided a method for producing a platelet lysate, the method includes: collecting whole blood from a donor; allowing the collected whole blood to pass through a leukapheresis filter to remove leukocyte; flushing a rinsing liquid through the leukapheresis filter through which the whole blood has been allowed to pass, in a flow direction of the whole blood, to recover residual blood retained on the leukapheresis filter as a rinsate; centrifuging the rinsate to recover a platelet-containing liquid; centrifuging the whole blood from which leukocyte has been removed, to recover a platelet-containing liquid; acquiring a platelet concentrate that contains platelet from the platelet-containing liquid; freezing and thawing the platelet concentrate; centrifuging, following freezing and thawing, the platelet concentrate to recover the platelet lysate.

According to another aspect of the present invention, there is provided a system for producing a platelet lysate used for the method for producing a platelet lysate according to the aforementioned aspect, the system includes: a bag set including a concentration bag that pools the platelet concentrate, and a supernatant recovery bag connected through a coupling tube to the concentration bag; and a centrifuge including a centrifugal unit that applies a centrifugal force to the bag set, a pressing unit that pressurizes the concentration bag to transfer a supernatant in the concentration bag to the supernatant recovery bag, and a sensor that detects a state of transfer of the supernatant, the centrifuge transferring a specified amount of the supernatant, having been obtained by centrifuging the platelet concentrate in the concentration bag, into the supernatant recovery bag, and stopping the centrifugal unit.

According to a still another aspect of the present invention, there is provided a bag set used in the method for producing a platelet lysate according to the aforementioned aspect, the bag set includes: a platelet concentration bag provided with a connection tube, a transfer port, and a coupling tube; a transfer tube connected to the transfer port; and a supernatant recovery bag connected through the transfer tube to the platelet concentration bag.

According to still another aspect of the present invention, there is provided a bag set for recovering platelet from a leukapheresis filter, the bag set includes: a first whole blood bag that pools whole blood of a donor; a leukapheresis filter connected to a downstream side of the first whole blood bag; a second whole blood bag connected through the leukapheresis filter to a downstream side of the first whole blood bag; a recovery liquid bag connected to a downstream side of the leukapheresis filter, and pooling a platelet recovery liquid for recovering platelet from the leukapheresis filter; and a concentration bag set connected to an upstream side of the leukapheresis filter.

According to still another aspect of the present invention, there is provided a bag set for recovering platelet from a leukapheresis filter, the bag set includes: a first whole blood bag that pools whole blood of a donor; a leukapheresis filter connected to a downstream side of the first whole blood bag; a second whole blood bag connected through the leukapheresis filter to a downstream side of the first whole blood bag; a recovery liquid bag connected to an upstream side of the leukapheresis filter, and pooling a rinsing liquid for recovering residual blood from the leukapheresis filter; and a residual blood recovery bag connected to a downstream side of the leukapheresis filter.

According to the method for producing a platelet lysate, the production system, and the bag set according to the aforementioned aspects, a platelet lysate can be efficiently produced with a simple device structure. In addition, further concentration of the platelet concentrate, prior to freezing, can reduce (compress) the volume of the platelet concentrate to be frozen. Hence, even a small refrigeration facility can produce a platelet lysate collected from a large number of donors. Moreover, small volume of the highly concentrated platelet concentrate to be handled can ensure good workability.

DESCRIPTION OF EMBODIMENTS

Preferred embodiments of the present invention will be detailed below, referring to the attached drawings. Note although each bag used in the following embodiments is provided with a connection port (transfer port) to which a tube is connected, the connection port may have, at least in a part thereof, a click chip (easily tearable part) which can be snapped off or opened.

First Embodiment

The method for producing a platelet lysate of this embodiment is conducted typically at a blood center where blood collected from donors is processed to produce various blood products, by using a production system 10 that includes a centrifuge 18 and a refrigerated storage 20 installed in the blood center.

Figure 1:
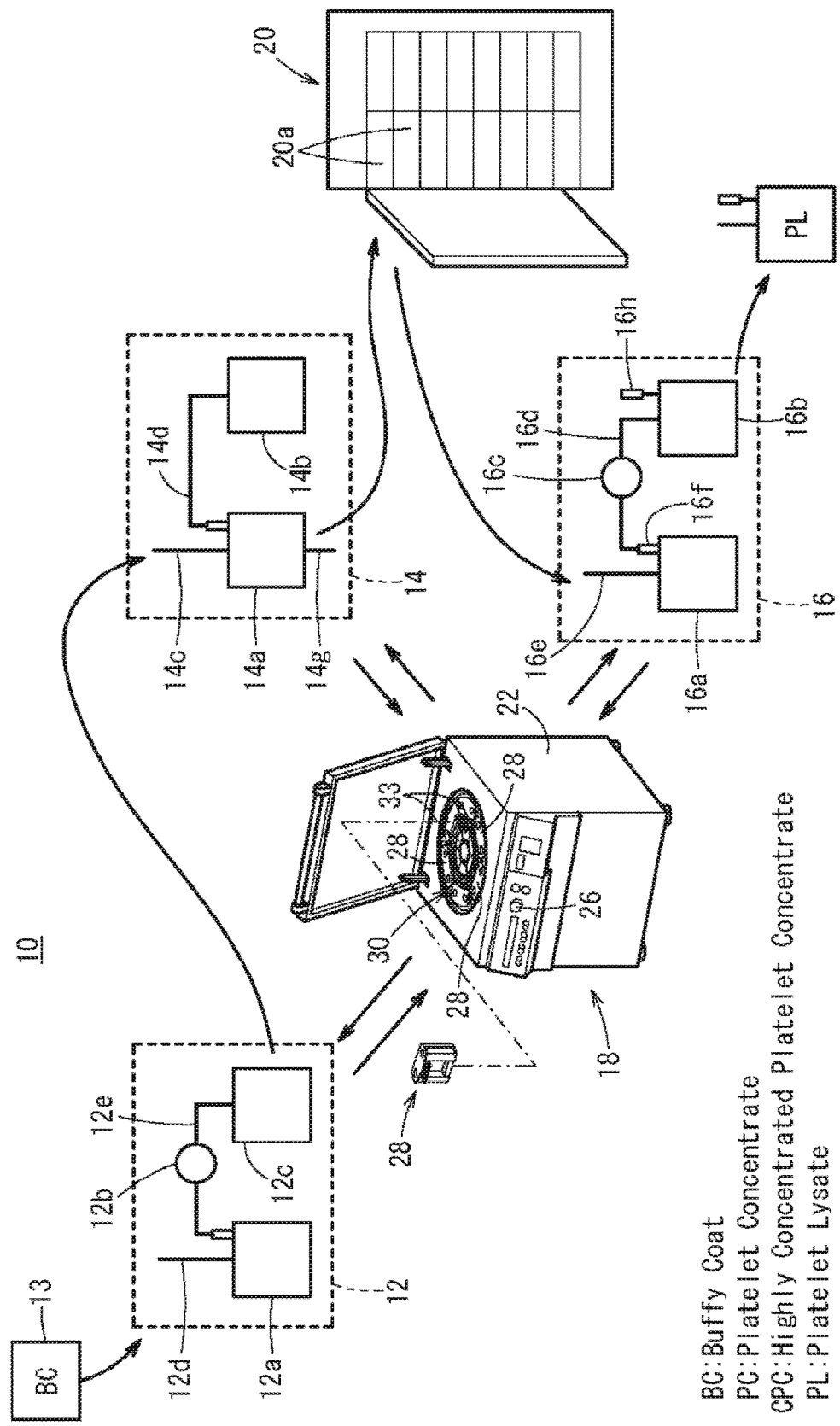
FIG. 1 is an explanatory drawing illustrating an overall structure of a system for producing a platelet lysate of a first embodiment.

As illustrated in FIG. 1, the production system 10 for producing a platelet lysate of this embodiment includes a platelet collection set 12, a concentration bag set 14, a recovery bag set 16, the centrifuge 18, and the refrigerated storage 20.

The platelet collection set 12 is used for removing leukocyte from buffy coat BC obtained by centrifuging whole blood WB to extract platelet concentrate PC, and is provided as a disposable product. The platelet collection set 12 includes a BC separation bag 12a, a leukapheresis filter 12b, and a PC recovery bag 12c.

Figure 6:
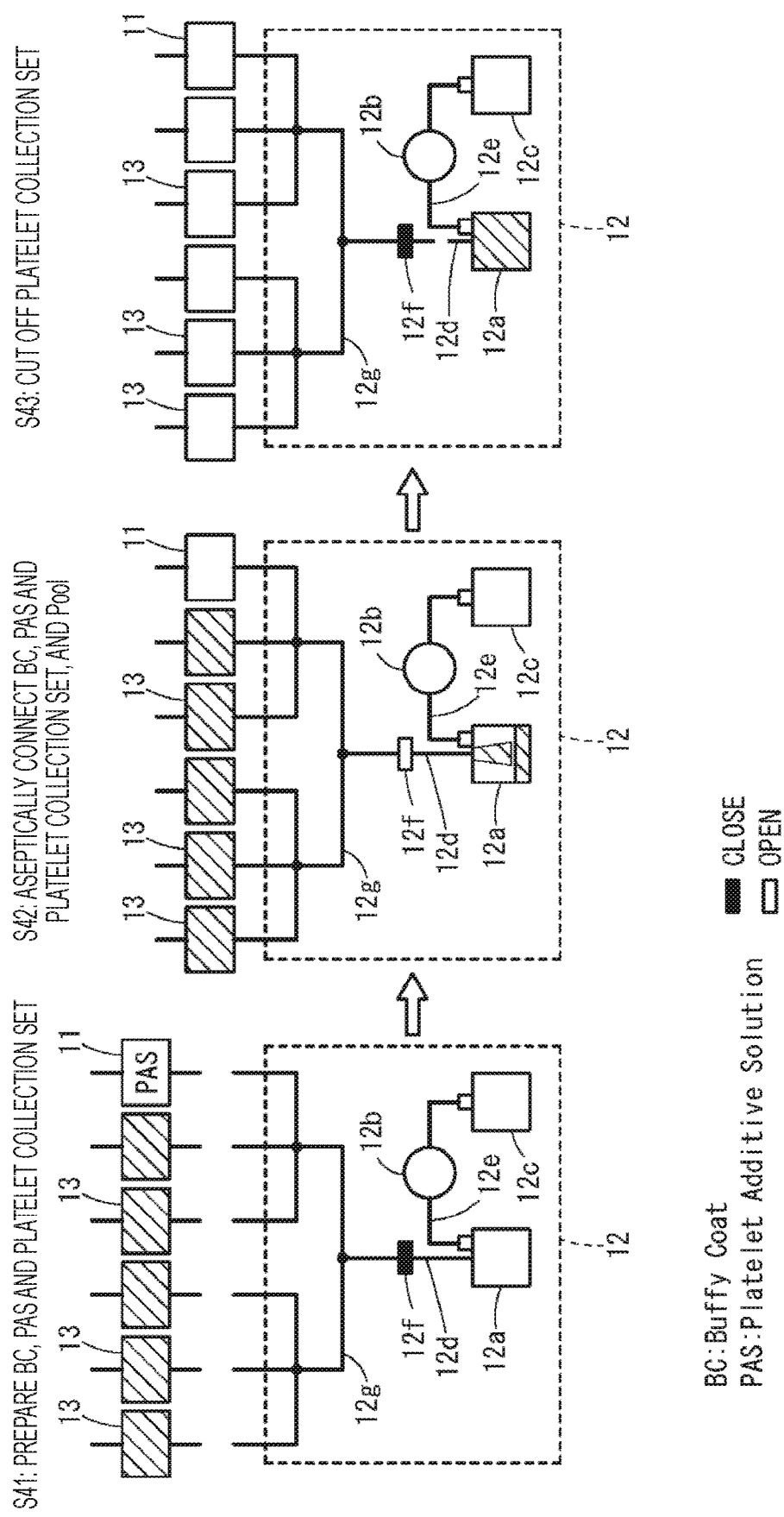
FIG. 6 is an explanatory drawing illustrating steps up to pooling of buffy coat in FIG. 5 in sequence.

The BC separation bag 12a is provided with a transfer tube 12d and a transfer tube 12e. As illustrated in FIG. 6, the transfer tube 12d is connected to a branch 12g through a clamp 12f, and is connected through the branch 12g to a plurality of BC bags 13. That is, the transfer tube 12d constitutes a flow channel through which the buffy coat BC pooled in the BC bags 13 is transferred to the BC separation bag 12a.

The transfer tube 12e communicates the BC separation bag 12a and the PC recovery bag 12c. The transfer tube 12e constitutes a flow channel through which the platelet concentrate PC, which is a supernatant obtained by centrifuging the buffy coat BC, is transferred to the PC recovery bag 12c. The leukapheresis filter 12b is provided on the way of the transfer tube 12e. The leukapheresis filter 12b is given to remove leukocyte that remains in the supernatant being transferred.

The BC separation bag 12a has a capacity enough to pool the buffy coat BC collected from a plurality of donors. Although not particularly limited, this embodiment will be explained referring to an exemplary case where a single BC separation bag 12a pools the buffy coats BC collected from five donors. This case may employ the BC separation bag 12a typically with a capacity of approximately 600 ml.

The PC recovery bag 12c is devised to communicate with the BC separation bag 12a through the transfer tube 12e, and is devised to pool the platelet concentrate PC separated by the BC separation bag 12a. The PC recovery bag 12c adoptable here typically has a capacity of approximately 600 ml.

Figure 2:
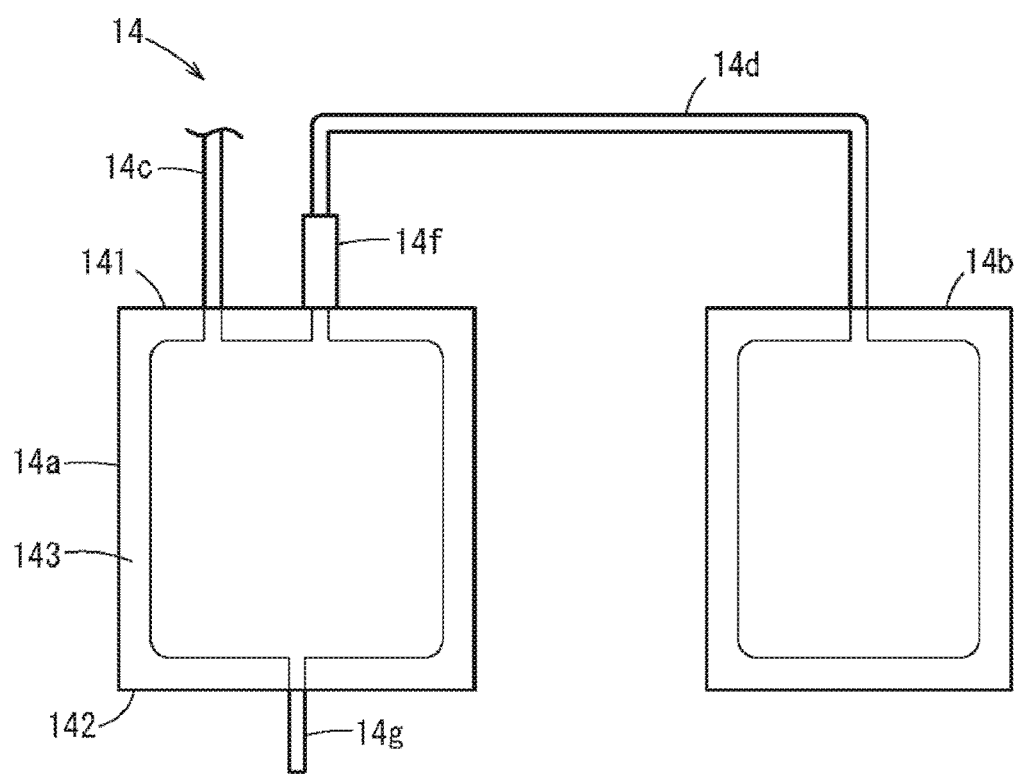
FIG. 2 is a plan view illustrating a concentration bag set.

As illustrated in FIG. 2, the concentration bag set 14 is used for concentrating the platelet concentrate PC to extract the highly concentrated platelet concentrate CPC, and is provided as a disposable product. The concentration bag set 14 includes a PC concentration bag 14a, a supernatant recovery bag 14b, and a transfer tube 14d that connects the PC concentration bag 14a and the supernatant recovery bag 14b.

The PC concentration bag 14a is devised to transfer the platelet concentrate PC pooled in the PC recovery bag 12c, and to concentrate the platelet concentrate PC while being set on the centrifuge 18. The PC concentration bag 14a is a container formed by superposing a pair of rectangular resin sheets, and sealing the circumference 143. A connection tube 14c and a transfer port 14f extend from one end 141 of the PC concentration bag 14a. A coupling tube 14g extends from the other end 142 opposite to the one end 141.

The connection tube 14c and the coupling tube 14g communicate with the inside of the PC concentration bag 14a. In a shipping form, the end of the connection tube 14c and the end of the coupling tube 14g are sealed by welding. The connection tube 14c or the coupling tube 14g is optionally connectable to other tube, by using an unillustrated aseptic joint.

The connection tube 14c is connected to the PC recovery bag 12c in FIG. 1 and serves as a flow channel through which the platelet concentrate PC in the PC recovery bag 12c is transferred. The connection tube 14c is also connected to the coupling tube 14g of another PC concentration bag 14a, and serves as a flow channel through which the highly concentrated platelet concentrate CPC is transferred to the recovery bag set 16. The coupling tube 14g is connected to another PC concentration bag 14a to form a flow channel through which the highly concentrated platelet concentrate CPC is transferred.

The transfer tube 14d is connected to the transfer port 14f of the PC concentration bag 14a. Through the transfer tube 14d, the PC concentration bag 14a and the supernatant recovery bag 14b communicate with each other. The transfer tube 14d forms a flow channel through which the supernatant of the platelet concentrate PC, produced in the PC concentration bag 14a after being centrifuged, is transferred to the supernatant recovery bag 14b. The transfer tube 14d is allowed for attachment of a clamp 34 (see FIG. 4) of the centrifuge 18, a sensor 32, a pump and so forth described later.

The supernatant recovery bag 14b recovers the supernatant of the platelet concentrate PC. After completion of concentration of the platelet concentrate PC, the transfer tube 14d is cut, whereby the supernatant recovery bag 14b is separated from the PC concentration bag 14a and collected. The PC concentration bag 14a separated from the supernatant recovery bag 14b is subjected to freezing process in the refrigerated storage 20, followed by thawing process. The supernatant in the supernatant recovery bag 14b is plasma which may be used as raw plasma.

Capacity of the PC concentration bag 14a and the supernatant recovery bag 14b may be equivalent to the capacity of the PC recovery bag 12c. Although not particularly limited, in a case where the buffy coats BC collected from five donors are handled as one lot, a capacity of approximately 300 ml will suffice for the PC concentration bag 14a and the supernatant recovery bag 14b. In this case, the platelet concentrate PC pooled in the PC concentration bag 14a will amount approximately 250 ml, and the volume of the highly concentrated platelet concentrate CPC that remains in the PC concentration bag 14a after concentration will be reduced to approximately 25 ml.

Figure 3:
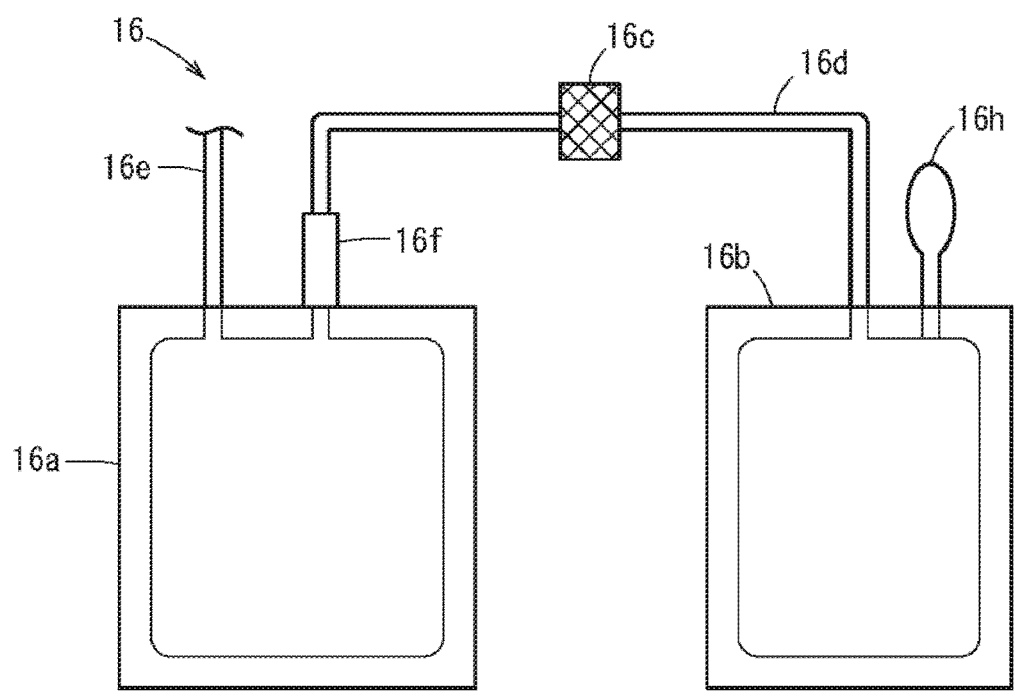
FIG. 3 is a plan view illustrating a recovery bag set.

As illustrated in FIG. 3, the recovery bag set 16 is used to separate and recover the platelet lysate PL from the highly concentrated platelet concentrate CPC having been frozen and thawed, and is provided as a disposable product. The recovery bag set 16 includes a PL separation bag 16a, a PL recovery bag 16b that recovers the platelet lysate PL, and a transfer tube 16d that connects the PL separation bag 16a and the PL recovery bag 16b.

The PL separation bag 16a is devised to pool the highly concentrated platelet concentrate CPC pooled in the plurality of PC concentration bags 14a, to separate the platelet lysate PL from residue of platelet membrane. The PL separation bag 16a, which is intended for use in the freezing and thawing processes, is preferably composed of a material unbreakable in the freezing and thawing processes. Hence as the material of the PL separation bag 16a, ethylene-vinyl acetate copolymer (EVA) resin is more preferred over polyvinyl alcohol (PVC) resin having been used for ordinary blood bag or the like. EVA resin is suitable for the PL separation bag 16a, also since it is, by its nature, less likely to have plasma proteins adsorbed thereon.

Figure 10:
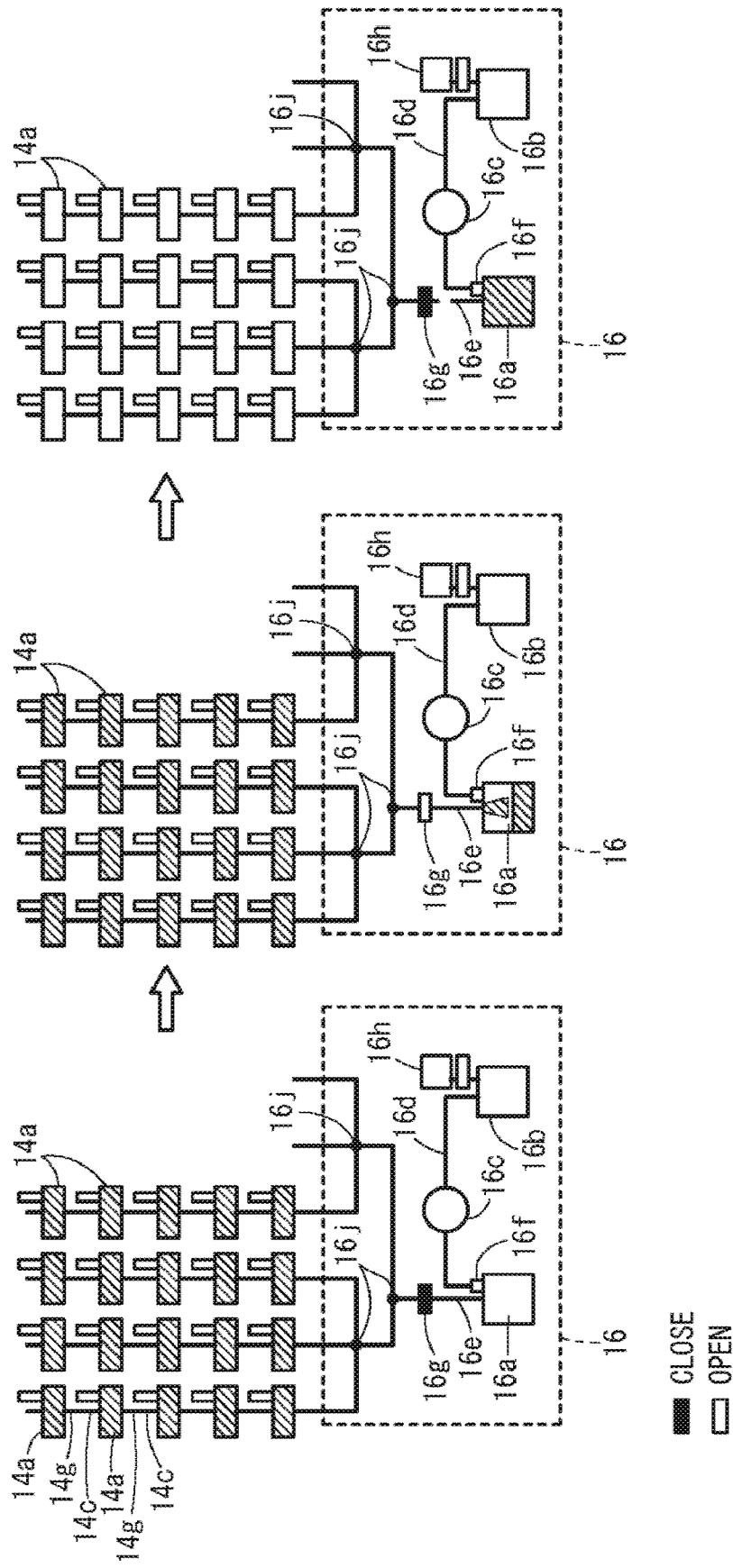
FIG. 10 is an explanatory drawing illustrating steps up to pooling of highly concentrated platelet concentrate in sequence.

The PL separation bag 16a is further provided with a connection tube 16e and a transfer port 16f. As illustrated in FIG. 10, the connection tube 16e is connected to the plurality of PC concentration bags 14a through branches 16j, and forms a flow channel through which the highly concentrated platelet concentrate CPC in the PC concentration bags 14a is transferred to the PL separation bag 16a. As illustrated in FIG. 3, a transfer tube 16d is connected to the transfer port 16f. That is, the PL separation bag 16a and the PL recovery bag 16b communicate with each other through the transfer tube 16d.

The transfer tube 16d forms a flow channel through which the platelet lysate PL, which is a supernatant of the highly concentrated platelet concentrate CPC centrifuged in the PL separation bag 16a, is transferred. The transfer tube 16d is also provided with a foreign substance removal filter 16c for removing foreign substances (approximately 0.2 μm) such as viruses contained in the platelet lysate PL, whereby the platelet lysate PL, from which the foreign substances have been removed by the foreign substance removal filter 16c, is recovered in the PL recovery bag 16b.

The PL recovery bag 16b recovers the platelet lysate PL. The PL recovery bag 16b may be provided with a sampling pouch 16h for sampling the content.

An ordinary blood bag is applicable to the PL separation bag 16a and the PL recovery bag 16b. In an exemplary case where the highly concentrated platelet concentrate CPC in twenty PC concentration bags 14a (that is, contributed by 100 donors) is pooled, the PL separation bag 16a and the PL recovery bag 16b may have a nominal capacity of 600 ml.

The centrifuge 18, as illustrated in FIG. 1, is a device repeatedly used in the process of producing the platelet lysate PL. The centrifuge 18 includes a box-shaped device body 22, and a rotor 30 (centrifugal unit) rotatably provided in the device body 22.

The device body 22 functions to internally or externally hold each bag of the platelet collection set 12, the concentration bag set 14 and the recovery bag set 16, and to control centrifugation of a predetermined component in each bag.

The device body 22 has a control unit 26 that accepts operation for centrifugation, displays the mode of operation, and controls operation of the individual units. The platelet collection set 12, the concentration bag set 14, and the recovery bag set 16 are housed in an insert unit 28 and then set in the rotor 30.

Figure 4:
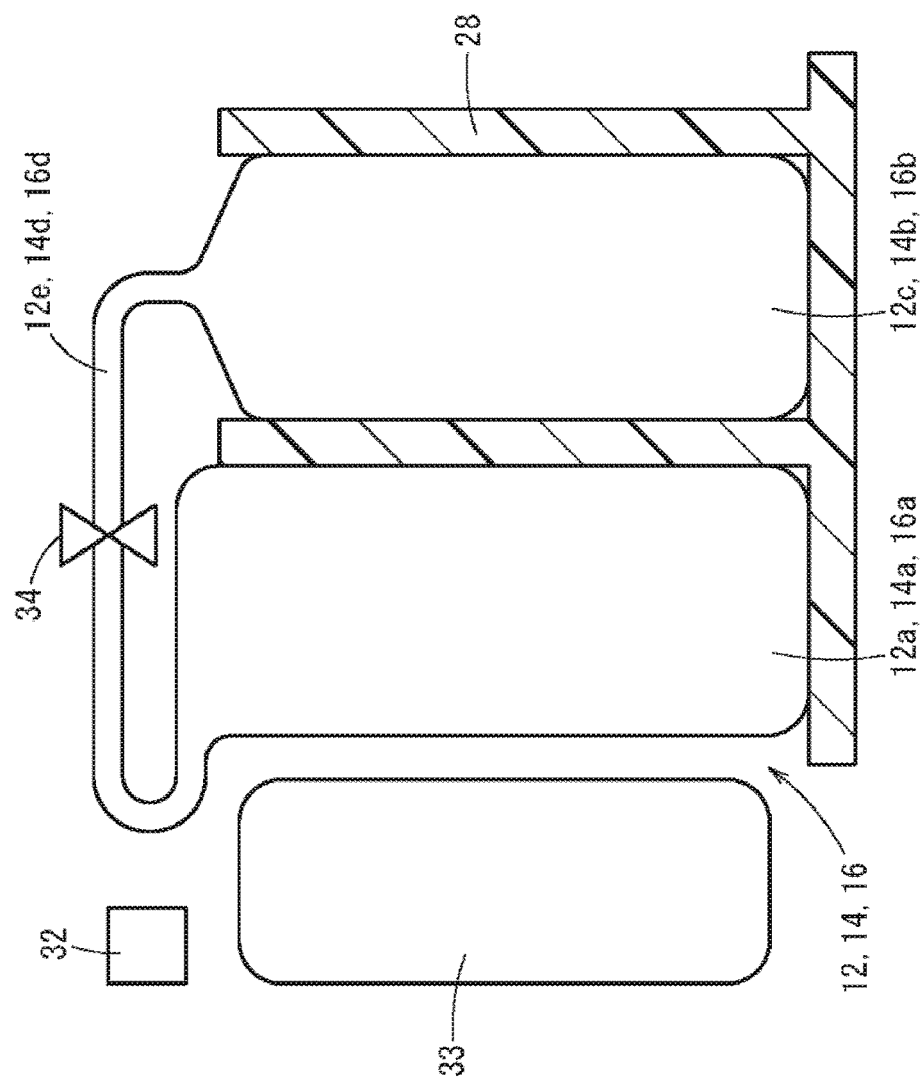
FIG. 4 is a cross-sectional view illustrating a centrifuge.

The insert unit 28 has, as illustrated in FIG. 4, the sensor 32, a clamp 34, and a pump (not illustrated) attached thereto. The insert unit 28 has also arranged thereto a pressing unit 33 that presses the platelet collection set 12, the concentration bag set 14 and the recovery bag set 16. The sensor 32 detects a state of transfer of a predetermined component through the transfer tubes 12e, 14d and 16d. The sensor 32 may detect changes in light transmittance of the transfer tubes 12e, 14d and 16d. The sensor 32 may alternatively detect displacement of the pressing unit 33 described later.

The rotor 30 of the device body 22 is formed in a cylindrical shape, as illustrated in FIG. 1, and is circumferentially divided into a plurality of sections, into each of which the insert unit 28 is loaded. The rotor 30 is provided, at the bottom thereof, with an unillustrated rotary drive source for rotating the rotor 30. The rotor 30 is also provided, at a part thereof adjoining to the inner circumferential side of the insert unit 28, with the pressing unit 33 that presses the platelet collection set 12, the concentration bag set 14 and the recovery bag set 16 attached to the insert unit 28.

The insert unit 28 is made detachable from the rotor 30, and is allowed for easy attachment of the platelet collection set 12, the concentration bag set 14, and the recovery bag set 16. The individual units of the centrifuge 18 operate under control of the control unit 26.

The refrigerated storage 20 has, as illustrated in FIG. 1, a plurality of storage sections 20a. Each storage section 20a houses a plurality of PC concentration bags 14a whose content has been reduced by concentration. In the refrigerated storage 20, the freezing process of the highly concentrated platelet concentrate CPC takes place.

The platelet lysate production system 10 of this embodiment is thus constructed. Hereinafter, the method for producing a platelet lysate of this embodiment will be explained.

Figure 5:
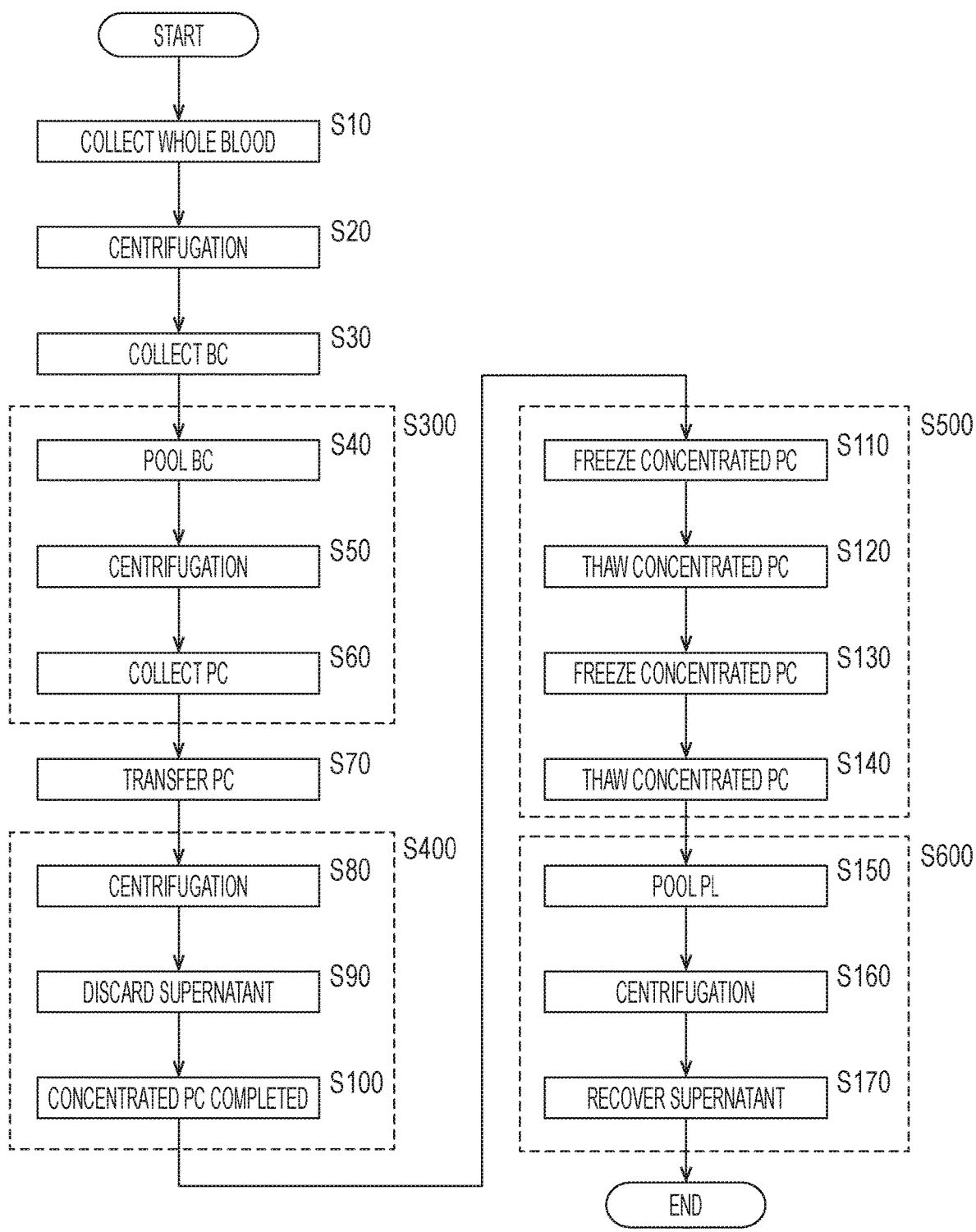
FIG. 5 is a flowchart illustrating a method for producing a platelet lysate according to the first embodiment.

The method for producing a platelet lysate is conducted according to the procedure illustrated in the flowchart of FIG. 5. First, in step S10, whole blood is collected by a medical worker such as doctor or nurse. Then in step S20, the collected blood is centrifuged by using the centrifuge 18 installed in a medical facility, a bloodmobile, a blood center or the like. During centrifugation, erythrocyte, platelet, leukocyte and plasma in the whole blood WB will separate according to their specific gravities. The whole blood WB is therefore separated into concentrated erythrocyte, plasma, and buffy coat BC that appears between the concentrated erythrocyte and the plasma (step S30). The buffy coat BC mainly contains platelet and leukocyte.

Then in step S300, the leukocyte is removed from the buffy coat BC to collect the platelet concentrate PC. First in step S40, the buffy coats BC collected from a plurality of donors are pooled. That is, as illustrated in step S41 in FIG. 6, the platelet collection set 12, a plurality of BC bags 13 that contain the buffy coats BC, and a PAS bag 11 that contains platelet additive solution (PAS) are prepared.

Next in step S42, the BC bags 13 and the PAS bag 11 are aseptically connected to the BC separation bag 12a of the platelet collection set 12. The clamp 12f is then opened, and the buffy coats BC and the platelet additive solution PAS are pooled in the BC separation bag 12a. Pooling of the buffy coats BC from a plurality of donors can suppress variation among the buffy coats BC.

Thereafter, in step S43, the transfer tube 12d is cut to separate the BC bags 13 and the PAS bag 11, from the platelet collection set 12.

Figure 7:
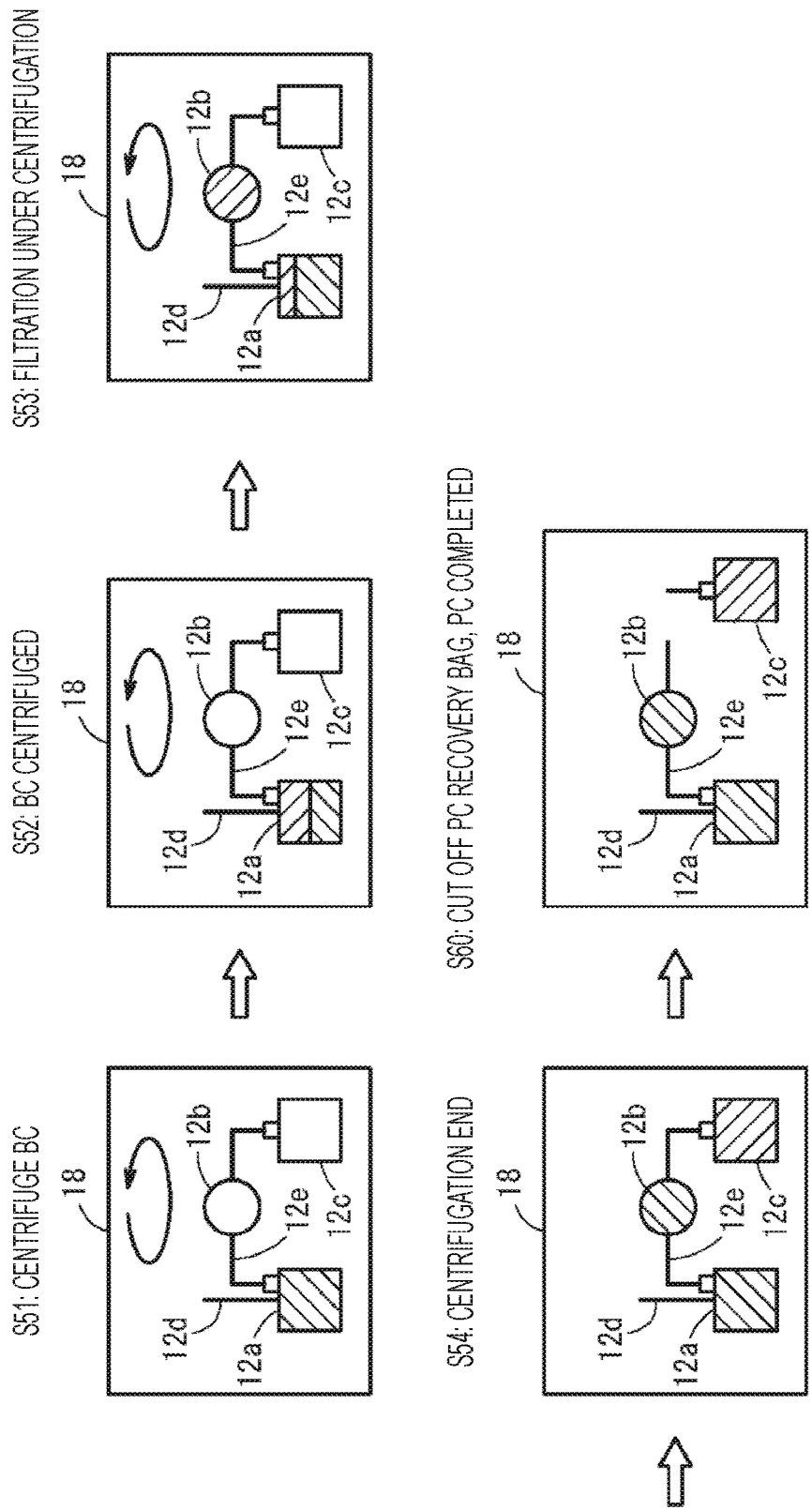
FIG. 7 is an explanatory drawing illustrating steps up to collection of platelet concentrate in sequence.

Next, in step S50 in FIG. 5, the buffy coat BC pooled in the platelet collection set 12 is centrifuged on the centrifuge 18. That is, as illustrated in step S51 in FIG. 7, the platelet collection set 12 is set on the centrifuge 18, and a centrifugal force is applied to the BC separation bag 12a. The buffy coat BC in the BC separation bag 12a is consequently separated, as illustrated in step S52, into a suspension that contains erythrocyte and leukocyte, and a supernatant which is a plasma (platelet-rich plasma) rich in platelet.

Next as illustrated in step S53, the supernatant in the BC separation bag 12a is transferred to the PC recovery bag 12c, while applying the centrifugal force by rotating the rotor 30 of the centrifuge 18. When transferred through the transfer tube 12e to the PC recovery bag 12c, the supernatant in the BC separation bag 12a passes through the leukapheresis filter 12b. This removes the leukocyte that remains in the supernatant. The platelet concentrate PC is thus recovered in the PC recovery bag 12c.

As illustrated in step S54, the centrifuge 18 stops the operation of the centrifugal unit upon detection, by the sensor 32, of leakage of erythrocyte from the BC separation bag 12a. Then in step S60, the platelet collection set 12 is taken out from the centrifuge 18, and the PC recovery bag 12c is separated by cutting from the BC separation bag 12a, thereby completing collection of the platelet concentrate PC.

Figure 8:
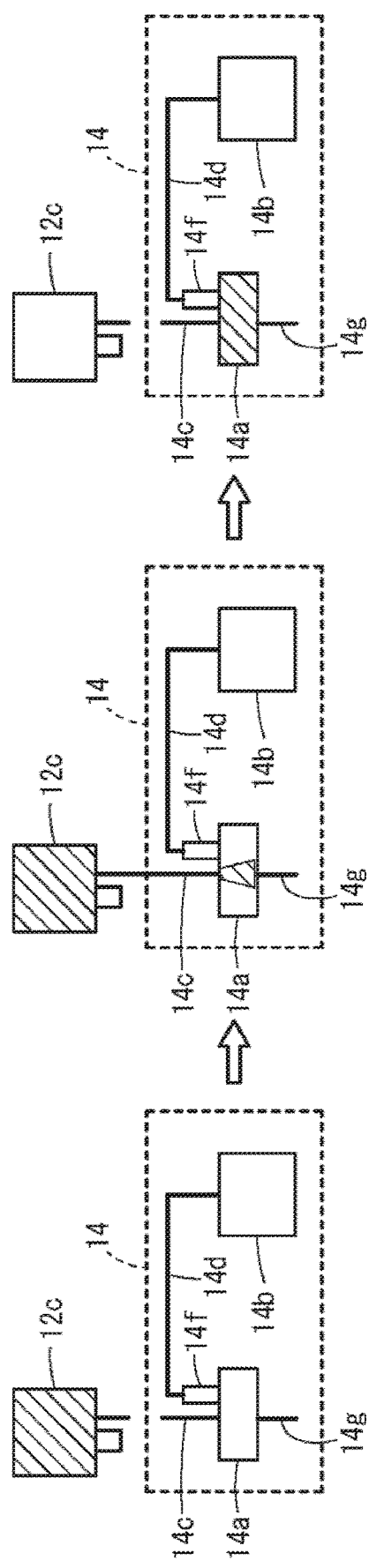
FIG. 8 is an explanatory drawing illustrating steps up to transfer of platelet concentrate in sequence.

Next in step S70 in FIG. 5, the platelet concentrate PC collected in step S60 is transferred to the concentration bag set 14. That is, as illustrated in step S71 in FIG. 8, the concentration bag set 14 and the PC recovery bag 12c that pools the platelet concentrate PC are prepared.

Next, in step S72, the PC recovery bag 12c and the PC concentration bag 14a are aseptically connected through the connection tube 14c. The platelet concentrate PC in the PC recovery bag 12c is then transferred to the PC concentration bag 14a.

Next, in step S73, the connection tube 14c is cut to separate the PC recovery bag 12c. Thus, the transfer process in step S70 in FIG. 5 is completed.

Figure 9:
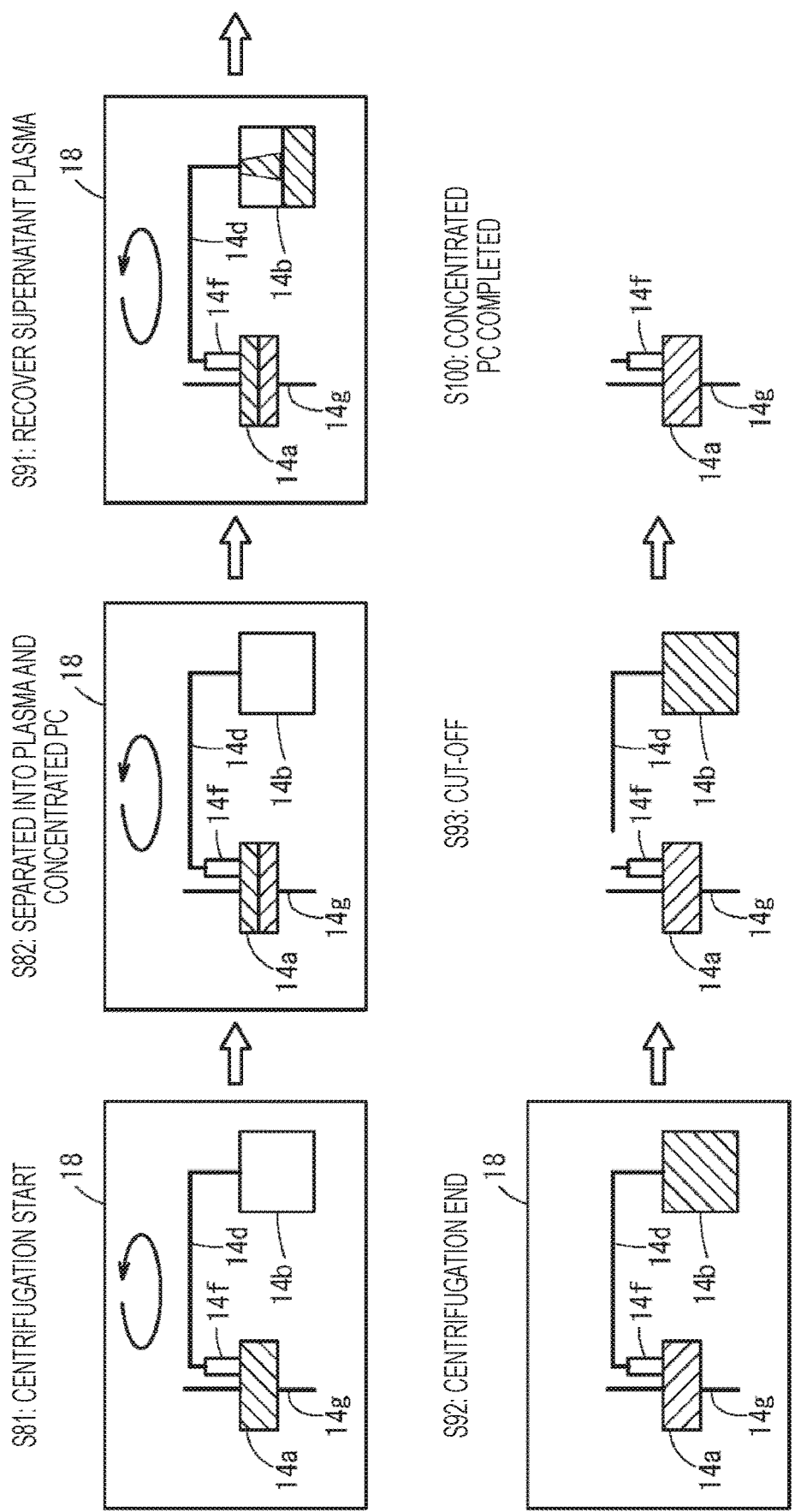
FIG. 9 is an explanatory drawing illustrating steps up to preparation of highly concentrated platelet concentrate in sequence.

Next, in step S400, a highly concentrated platelet concentrate CPC is prepared. First, in step S80, the platelet concentrate PC is centrifuged. That is, in step S81 of FIG. 9, the concentration bag set 14 is set on the centrifuge 18, and the rotor 30 of the centrifuge 18 is rotated to apply centrifugal force to the PC concentration bag 14a of the concentration bag set 14. Consequently as illustrated in step S82, the platelet concentrate PC in the PC concentration bag 14a is separated into plasma rich in water, and highly concentrated platelet concentrate (CPC) rich in platelet. The plasma is separated as a supernatant.

Next, the process advances to step S90 in FIG. 5, where the plasma is recovered. That is, in step S91 in FIG. 9, the centrifuge 18 drives the pressing unit 33 to press the PC concentration bag 14a while keeping the centrifugal unit (rotor 30) operated, thereby transferring the supernatant plasma to the supernatant recovery bag 14b. Then in step S92, the centrifuge 18 detects the state of transfer of the plasma to the supernatant recovery bag 14b, or displacement of the pressing unit 33 with use of the sensor 32, and stops the operation of the centrifugal unit.

Then in step S93, the concentration bag set 14 is detached from the centrifuge 18. Then, in step S100, the transfer tube 14*d* is cut to separate the supernatant recovery bag 14*b* from the PC concentration bag 14*a*. The PC concentration bag 14*a* has left therein the platelet concentrate, whereby concentration of platelet in the PC concentration bag 14*a* comes to the end. The volume of the highly concentrated platelet concentrate CPC in the PC concentration bag 14*a* is reduced down to approximately ¹⁄₁₀ of the volume of the original platelet concentrate PC. The concentration of the platelet concentrate PC in step S400 in FIG. 5 is thus completed.

Next, in step S500 in FIG. 5, the highly concentrated platelet concentrate CPC is frozen and thawed. That is, steps S110 and S130 for storing the PC concentration bag 14*a* in the refrigerated storage 20 thereby freezing the highly concentrated platelet concentrate CPC, and steps S120 and S140 for thawing the frozen highly concentrated platelet concentrate CPC, are alternately conducted a plurality of times. Although illustrated as being repeated twice, the number of times of freezing and thawing are not limited thereto, and each may be conducted only once. Alternatively, the freezing and thawing may be repeated three or more times. With the freezing and thawing repeated a plurality of times, platelet membrane may be more thoroughly broken, thereby desirably improving the yield of the platelet lysate PL.

Next, in step S600, the platelet lysate PL having been frozen and thawed is recovered. First, in step S150, the highly concentrated platelet concentrate CPC having been frozen and thawed is pooled. That is, as illustrated in step S151 in FIG. 10, a plurality of PC concentration bags 14*a* and a recovery bag set 16 are prepared. The plurality of PC connection bags 14*a* are connected in series, by connecting the coupling tube 14*g* of the PC concentration bag 14*a* to the connection tube 14*c* of another PC concentration bag 14*a*. This enables connection of a large number of PC concentration bags 14*a* without increasing the number of branches. Furthermore, a plurality of groups of the series-connected PC concentration bags 14*a* are prepared.

Next, in step S152, a plurality of groups of PC concentration bags 14*a* are connected through branches 16*j* to the recovery bag set 16. A clamp 16*g* is then opened to pool the highly concentrated platelet concentrate CPC having been frozen and thawed in the PC concentration bags 14*a*, into the PL separation bag 16*a* of the recovery bag set 16. In the illustrated example, the highly concentrated platelet concentrate CPC having been frozen and thawed in twenty PC concentration bags 14*a* is pooled in the PL separation bag 16*a*. This means that the highly concentrated platelet concentrate CPC contributed by 100 donors, having been frozen and thawed, can be pooled in the PL separation bag 16*a*, thus achieving homogenized quality.

Next, in step S153, the connection tube 16*e* is cut, to separate the PC concentration bags 14*a* from the recovery bag set 16. The pooling process of the highly concentrated platelet concentrate CPC having been frozen and thawing, in step S150 in FIG. 5, is thus completed.

Figure 11:
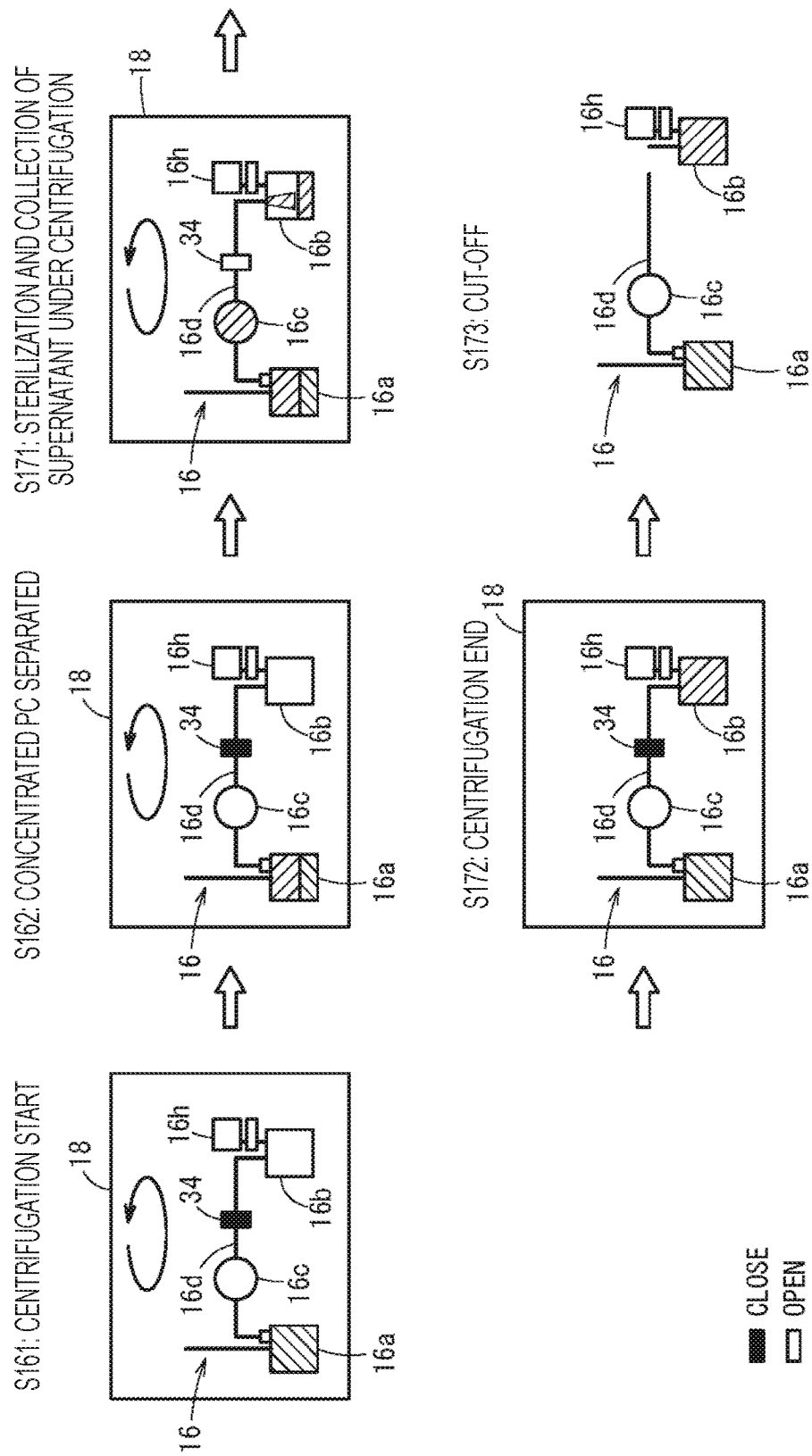
FIG. 11 is an explanatory drawing illustrating steps up to collection of platelet lysate in sequence.

Next, in step S160 in FIG. 5, the highly concentrated platelet concentrate CPC having been frozen and thawed is centrifuged. That is, in step S161 in FIG. 11, the recovery bag set 16 is set on the centrifuge 18, and the centrifuge 18 is operated to apply centrifugal force to the PL separation bag 16*a*. Consequently as illustrated in step S162, the highly concentrated platelet concentrate CPC having been frozen and thawed in the PL separation bag 16*a* is separated into a residue of the cell membrane and a supernatant composed of the platelet lysate PL.

Next, in step S170 in FIG. 5, the supernatant is recovered. That is, in step S171 in FIG. 11, the centrifuge 18 presses the PL separation bag 16*a*, while keeping the centrifugal force applied to the PL separation bag 16*a*. The supernatant composed of the platelet lysate PL is consequently transferred through the transfer tube 16*d* to the PL recovery bag 16*b*. In this process, the supernatant composed of the platelet lysate PL is sterilized (including removal of foreign substances such as virus) as a result of passage through the foreign substance removal filter 16*c*.

Thereafter, in step S172, the centrifuge 18 recovers a specified volume of platelet lysate PL into the PL recovery bag 16*b*, and then stops the operation.

Then as illustrated in step S173, the recovery bag set 16 is detached from the centrifuge 18, and the PL recovery bag 16*b* is cut off to recover the platelet lysate PL. Production of the platelet lysate PL of this embodiment is thus completed. The PL recovery bag 16*b* pools, for example, the platelet lysate PL contributed by 100 donors.

The method for producing a platelet lysate, the production system 10, and the recovery bag set 16 of this embodiment described above demonstrate the following effects.

According to the method for producing a platelet lysate of this embodiment, the platelet concentrate PC is concentrated before being frozen. This enables reduction of volume of the highly concentrated platelet concentrate CPC in the PC concentration bag 14*a* to be frozen, making it possible to subject platelet collected from a large number of donors to the freezing process, even in a small-scale refrigerated storage 20. Moreover, even when pooling the highly concentrated platelet concentrate CPC contributed by a large number of donors for recovery of platelet lysate PL, the method will excel in operability, since the volume will not be excessively large.

In the method for producing a platelet lysate, the steps (steps S70 and S400) of preparing the highly concentrated platelet concentrate CPC may include a step (step S70) of transferring the platelet concentrate PC contributed by a plurality of donors to the PC concentration bag 14*a*; a step (step S80) of setting the PC concentration bag 14*a* on the centrifuge 18, and centrifuging the platelet concentrate PC; and a step (step S90) of transferring, and thus removing, a supernatant in the PC concentration bag 14*a* to the supernatant recovery bag 14*b*. This enables removal of water (plasma), which accounts for the most part of platelet concentrate PC, thereby largely reducing the capacity of the PC concentration bags 14*a* to be put into the process.

In the method for producing a platelet lysate, the step of recovering the platelet lysate PL (step S600) may include a step of pooling the highly concentrated platelet concentrate CPC pooled in the plurality of PC concentration bags 14*a* in the PL separation bag 16*a* (step S150); a step of setting the PL separation bag 16*a* on the centrifuge 18 to separate the highly concentrated platelet concentrate CPC into a precipitate composed of a residue of cell membrane and a supernatant that contains the platelet lysate PL (step S160); and a step of recovering the supernatant that contains the platelet lysate PL in the PL recovery bag 16*b* (step S170). Pooling of the highly concentrated platelet concentrate CPC enables production of formulation by using platelet contributed by a large number of donors, even with use of a small-scale equipment. Homogenized quality may be thus achieved.

In the production of the platelet lysate, the step of freezing and thawing the highly concentrated platelet concentrate CPC may be repeated a plurality of times. This enables more effective breakage of platelet membrane, and efficient extraction of the platelet lysate PL.

The platelet lysate production system 10 of this embodiment may include: the concentration bag set 14 that includes the PC concentration bag 14a that pools the platelet concentrate PC, and the supernatant recovery bag 14b connected through the transfer tube 14d to the PC concentration bag 14a; and the centrifuge 18 that includes the rotor 30 that applies a centrifugal force to the concentration bag set 14, the pressing unit 33 that pressurizes the PC concentration bag 14a to transfer the supernatant in the PC concentration bag 14a to the supernatant recovery bag 14b, and the sensor 32 that detects volume of transfer of the supernatant. The centrifuge 18 may be devised to transfer a specified amount of the supernatant, having been obtained by centrifuging the platelet concentrate PC in the PC concentration bag 14a, into the supernatant recovery bag 14b, and then to stop the rotor 30. This enables concentration process of the platelet concentrate PC without manual intervention, whereby the productivity is improved.

The concentration bag set 14 of this embodiment includes the PC concentration bag 14a provided with the connection tube 14c, the transfer port 14f, and the coupling tube 14g; the transfer tube 14d connected to the transfer port 14f; and the supernatant recovery bag 14b connected through the transfer tube 14d to the PC concentration bag 14a. Provision of the coupling tube 14g, in addition to the connection tube 14c, enables series connection of the plurality of PC concentration bags 14a, thereby improving workability when recovering the platelet lysate PL.

In the concentration bag set 14, the PC concentration bag 14a may have the connection tube 14c and the transfer port 14f formed at one end, and may have the coupling tube 14g provided at the other end opposite to the connection tube 14c. In such structure with the plurality of PC concentration bags 14a connected in series, while arranging the connection tube 14c and the coupling tube 14g vertically, the highly concentrated platelet concentrate CPC may be easily gathered with the aid of gravity, whereby the workability is improved.

Second Embodiment

This embodiment will explain an exemplary case of the method for producing a platelet lysate having been described referring to FIGS. 1 to 11, with an additional step of removing the plasma component and coagulation factors from the highly concentrated platelet concentrate CPC with use of a rinsing liquid, in the step of concentrating the platelet concentrate PC (step S400).

Figure 12:
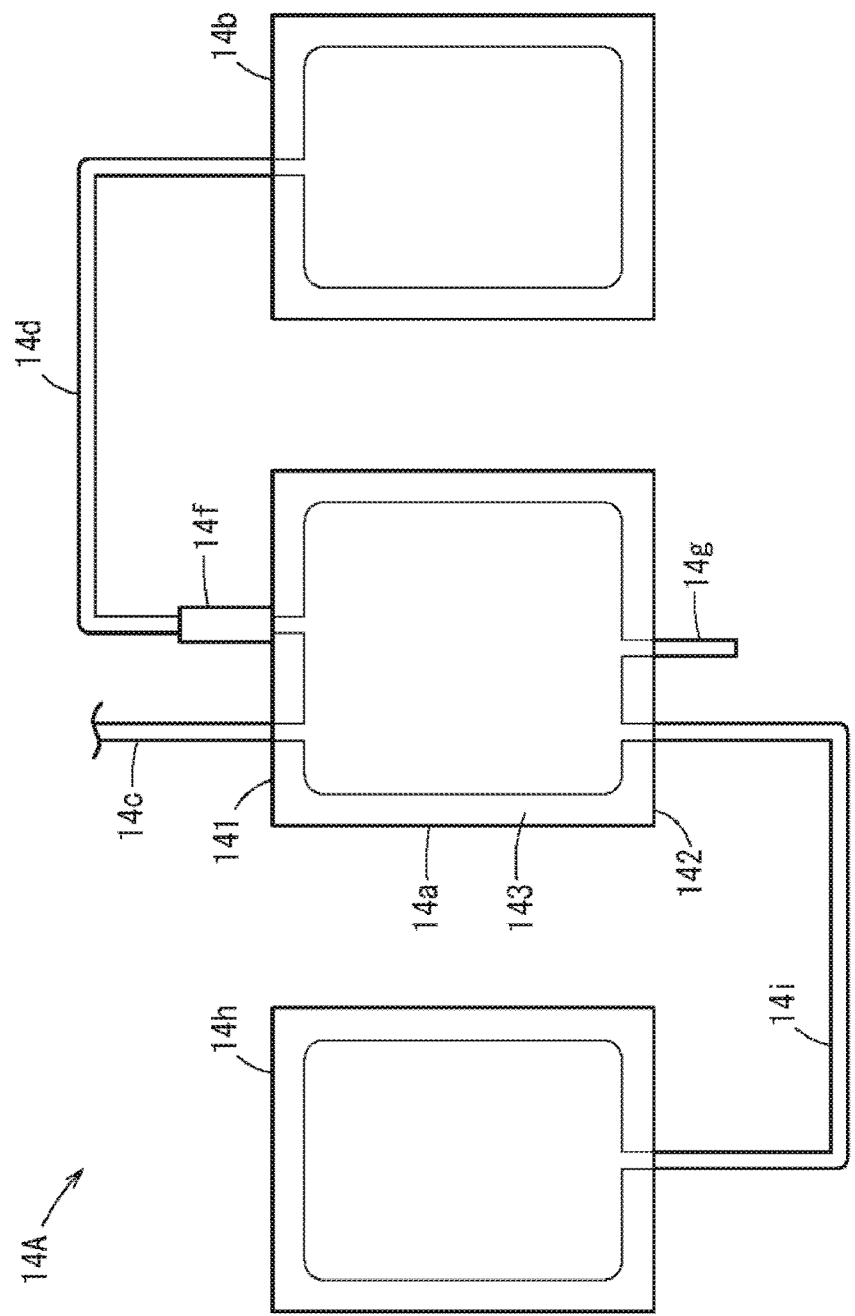
FIG. 12 is a plan view illustrating a concentration bag set according to a second embodiment.

As illustrated in FIG. 12, the concentration bag set 14A of this embodiment includes the PC concentration bag 14a, the supernatant recovery bag 14b, and additionally a rinsing liquid bag 14h. The rinsing liquid bag 14h pools a rinsing liquid which is composed of platelet additive solution PAS, saline or the like. The rinsing liquid bag 14h is connected through a rinsing liquid tube 14i to the PC concentration bag 14a. The rinsing liquid tube 14i is connected, as illustrated in the drawing, to the PC concentration bag 14a at the same end as the coupling tube 14g. That is, the rinsing liquid tube 14i is provided at the end opposite to the end where the transfer tube 14d is formed. When centrifuged, the separated highly concentrated platelet concentrate CPC is condensed towards the outer wall of the centrifuge. An effect of stirring the highly concentrated platelet concentrate CPC with the rinsing liquid is expectable, by introducing the rinsing liquid through the rinsing liquid tube 14i into the PC concentration bag 14a, during centrifugation.

The supernatant recovery bag 14b of this embodiment pools the rinsing liquid from the rinsing liquid bag 14h, together with the plasma separated from the PC concentration bag 14a. The supernatant recovery bag 14b therefore preferably has a capacity larger than the capacity of the PC concentration bag 14a, and the volume of the rinsing liquid pooled in the rinsing liquid bag 14h.

Figure 13:
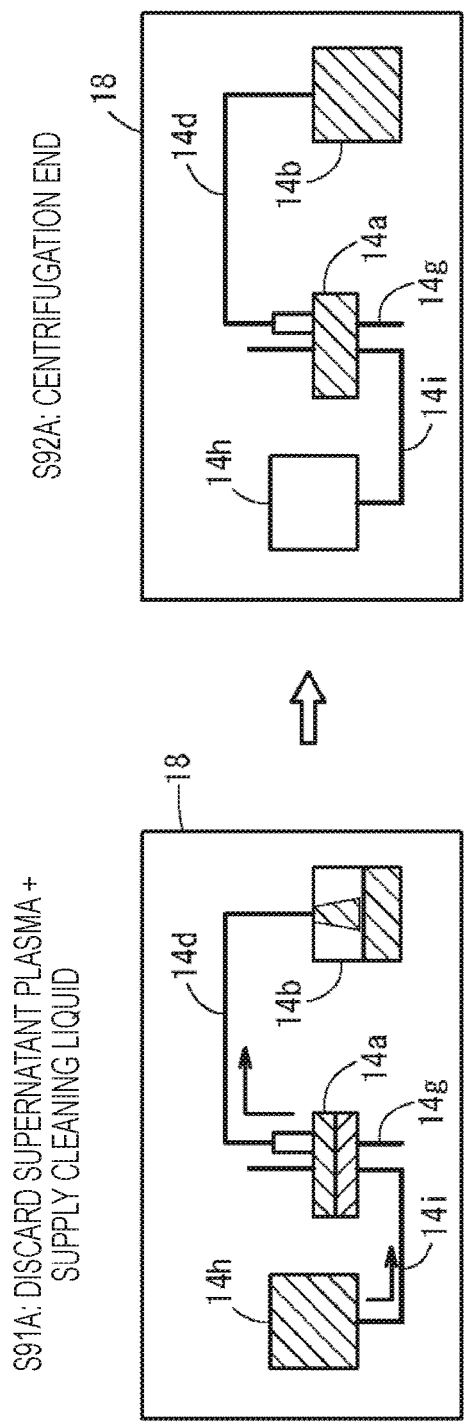
FIG. 13 is an explanatory drawing illustrating steps of concentration and rinsing of platelet concentrate according to the second embodiment in sequence.

Hereinafter, the method for producing a platelet lysate of this embodiment will be explained. The steps up to the step of setting the concentration bag set 14A on the centrifuge 18, and conducting centrifugation by applying a centrifugal force to the PC concentration bag 14a are the same as those in FIG. 8. Then in step S91A in FIG. 13, when recovering the separated supernatant, the rinsing liquid in the rinsing liquid bag 14h is fed into the PC concentration bag 14a, to rinse the highly concentrated platelet concentrate CPC. In this way, the plasma in the highly concentrated platelet concentrate CPC is replaced with the rinsing liquid, and coagulation factors such as fibrinogen in the highly concentrated platelet concentrate CPC are rinsed off with the rinsing liquid.

The rinsing liquid is transferred to the supernatant recovery bag 14b together with the separated plasma. The centrifuge 18 detects completion of the transfer of a specified volume of the rinsing liquid and plasma, on the basis of result of detection by the sensor 32, and stops the operation (step S92A). The concentration and rinsing steps of the platelet concentrate PC, in the method for producing a platelet lysate of this embodiment, are thus completed.

The method for producing a platelet lysate and the concentration bag set 14A of this embodiment described above demonstrate the following effects.

The method for producing a platelet lysate of this embodiment feeds the rinsing liquid to the PC concentration bag 14a to rinse the platelet concentrate PC, when centrifuging the platelet concentrate PC in the PC concentration bag 14a. In this way, the plasma in the platelet concentrate PC is replaced with the rinsing liquid, and coagulation factors such as fibrinogen are removed. Hence it becomes no longer necessary to add an anticoagulant such as heparin to the platelet lysate PL.

Moreover, the concentration bag set 14A of this embodiment further includes a rinsing liquid bag 14h that is connected through the rinsing liquid tube 14i to the PC concentration bag 14a, and supplies the rinsing liquid to the PC concentration bag 14a. This enables concentration and rinsing of the platelet concentrate PC.

Third Embodiment

The embodiments having been explained referring to FIGS. 1 to 13 relate to an exemplary mode where the buffy coat BC is separated from the whole blood WB collected from the donor, and the platelet concentrate PC is obtained from the buffy coat BC. The present invention is, however, not limited to these modes. The embodiment explained below will deal with the case where the platelet concentrate PC is directly collected by apheresis from the donor.

Figure 14:
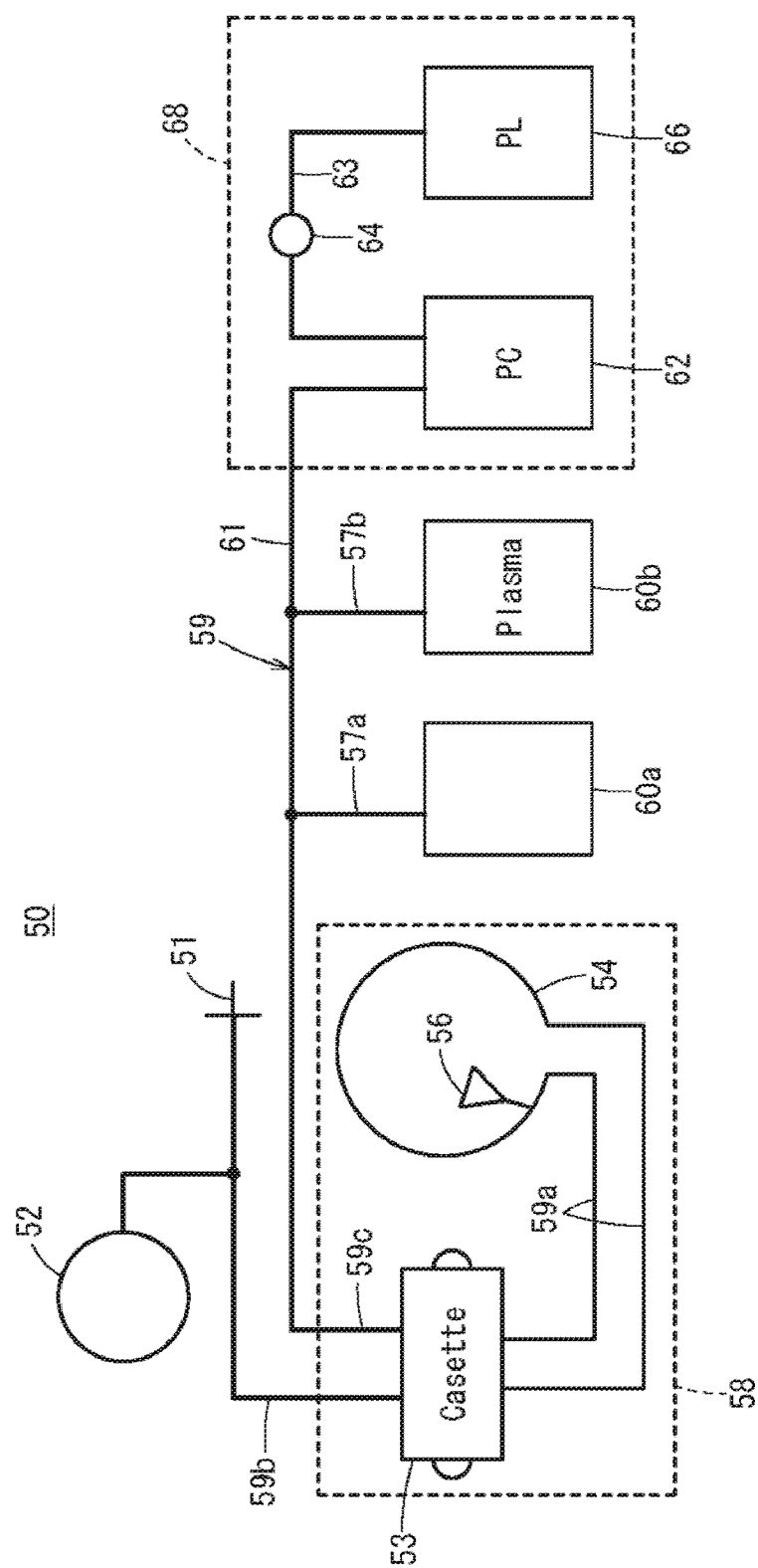
FIG. 14 is a block diagram illustrating a bag set according to a third embodiment.

For the method for producing a platelet lysate of this embodiment, a bag set 50 illustrated in FIG. 14 is used. The bag set 50 includes a blood separation chamber 54, a reservoir 60a, a plasma bag 60b, a concentration bag set 68, a tube 59 connecting them, a cassette 53 having the tube 59, laid in a predetermined path, held thereon or connected thereto, a blood collection unit 51 equipped with a puncture needle, and an initial flow blood bag 52. Among them, the cassette 53 is attached to the centrifuge 18 (see FIG. 1), as a centrifugal unit 58 of the blood separation chamber 54. The bag set 50 is disposable for one-time use, for contamination prevention and hygienic reasons.

The whole blood WB collected from the blood collection unit 51, from which the initial flow blood has been recovered in the initial flow blood bag 52, is introduced into the blood separation chamber 54. The blood separation chamber 54 is formed in a band-shaped bag, so as to be attachable to the rotor 30 of the centrifuge 18. The blood separation chamber 54 is a soft bag with a built-in blood separation unit to which the whole blood WB from the donor is fed, and is easily foldable. The whole blood WB introduced into the blood separation unit of the blood separation chamber 54 is centrifuged while it flows one end to the other end.

A leukapheresis chamber 56 is provided near one end of the blood separation chamber 54. The leukapheresis chamber 56 removes leukocyte from the whole blood WB that flows in the blood separation chamber 54, with the aid of centrifugal force. To the blood separation chamber 54, the cassette 53 is connected through a tube 59*a*.

The cassette 53 has also connected thereto a tube 59*b* and a tube 59*c*. The cassette 53 is connected through the tube 59*b* to the blood collection unit 51 and the initial flow blood bag 52. The cassette 53 is also connected through the tube 59*c* to the reservoir 60*a* and the concentration bag set 68. The tube 59*c* branches on the way into a tube 57*a* directed to the reservoir 60*a*, a tube 57*b* directed to the plasma bag 60*b*, and a tube 61 directed to the concentration bag set 68.

The concentration bag set 68 includes a platelet recovery bag 62, a platelet lysate bag 66, and a foreign substance removal filter 64. The tube 61 has connected thereto the platelet recovery bag 62 in which the platelet separated in the blood separation chamber 54 is pooled. The platelet recovery bag 62 is connected through the tube 63 to the platelet lysate bag 66. The tube 63 is provided with a foreign substance removal filter 64.

The whole blood WB introduced from the blood collection unit 51 is fed through the cassette 53 to the blood separation chamber 54. The whole blood WB is separated in the blood separation chamber 54, and the separated platelet is pooled in the platelet recovery bag 62 through the tube 61. Erythrocyte and plasma separated in the blood separation chamber 54 are respectively pooled in the reservoir 60*a* and the plasma bag 60*b*. From among the separated erythrocyte, a portion thereof beyond the capacity of the blood separation chamber 54 is pooled in the reservoir 60*a*. After completion of centrifugation, the erythrocyte is returned to the donor through the blood collection unit 51. The plasma pooled in the plasma bag 60*b* may be used as a raw material for formulation.

Figure 15:
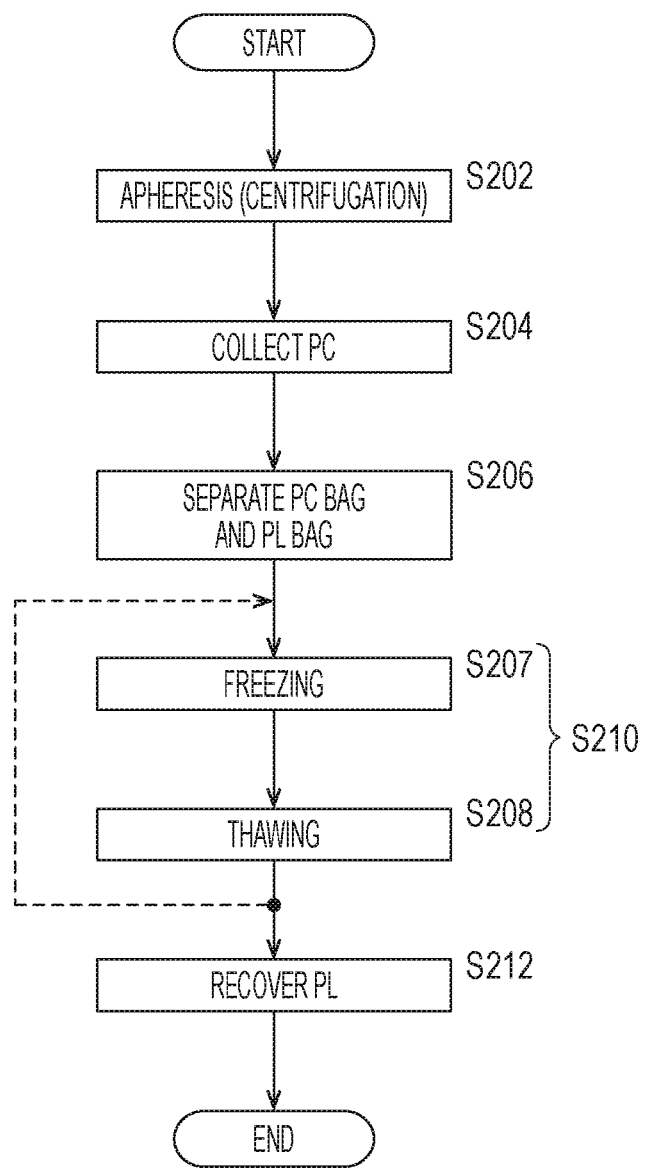
FIG. 15 is a flowchart illustrating a method for producing a platelet lysate according to a third embodiment.

Hereinafter, a method for producing a platelet lysate of this embodiment with use of the bag set 50 will be explained referring to FIG. 15.

First, blood is collected from the donor by apheresis (step S202). In the apheresis, blood (whole blood WB) is collected, by puncturing the donor with a puncture needle of the blood collection unit 51 of the bag set 50 illustrated in FIG. 14. After removing the initial flow blood by using the initial flow blood bag 52, the whole blood WB is fed to the blood separation chamber 54 of the centrifugal unit 58. In the blood separation chamber 54, the whole blood WB is separated into leukocyte, platelet, plasma, and erythrocyte. Among them, leukocyte is separated and removed in the leukapheresis chamber 56. Plasma is pooled in the plasma bag 60*b* through the tubes 59*a* and 59*c*, and the tube 57*b*. Erythrocyte is pooled in the reservoir 60*a* through the tubes 59*a* and 59*c*, and the tube 57*a*. The erythrocyte pooled in the reservoir 60*a* is then returned to the donor.

On the other hand, the platelet concentrate PC is pooled in the platelet recovery bag 62 of the concentration bag set 68 through the tubes 59*a*, 59*c* and 61 (step S204). In this embodiment, the platelet concentrate PC can be collected in the concentration bag set 68 directly from the donor. In the concentration bag set 68, the tube 63 is closed with a clamp or the like in the initial state, so that the platelet recovery bag 62 and the platelet lysate bag 66 do not communicate with each other.

Thereafter, the concentration bag set 68 is separated from the bag set 50 (step S206). The concentration bag set 68 is aseptically separated by cutting the tube 61, while concurrently closing the tube by heat welding with a high frequency welder (tube sealer).

The separated concentration bag set 68 is then cooled in a freezer to freeze the platelet concentrate PC in the platelet recovery bag 62 (step S207). Next, the concentration bag set 68 is returned to room temperature, to thaw the frozen platelet concentrate PC (step S208). The freezing and thawing processes (step S210) including the aforementioned steps S207 and S208 may be repeated a plurality of times. With the operation, platelet membrane is broken to produce the platelet lysate PL.

Next, the platelet lysate PL is recovered in the platelet lysate bag 66 (step S212). The concentration bag set 68 is set on the centrifuge 18 (see FIG. 1), to centrifuge the content of the platelet recovery bag 62. The platelet lysate PL is separated as a supernatant in the platelet recovery bag 62. Thereafter, the tube 63 is opened to make the platelet recovery bag 62 and the platelet lysate bag 66 communicate with each other, thereby transferring the supernatant in the platelet recovery bag 62 to the platelet lysate bag 66. While being transferred through the tube 63, the platelet lysate PL passes through the foreign substance removal filter 64, whereby any foreign substance is removed. The platelet lysate bag 66, with the platelet lysate PL recovered therein, is then aseptically separated, by closing the tube 61 under heat welding with a tube sealer. The production of the platelet lysate PL is thus completed.

Figure 16:
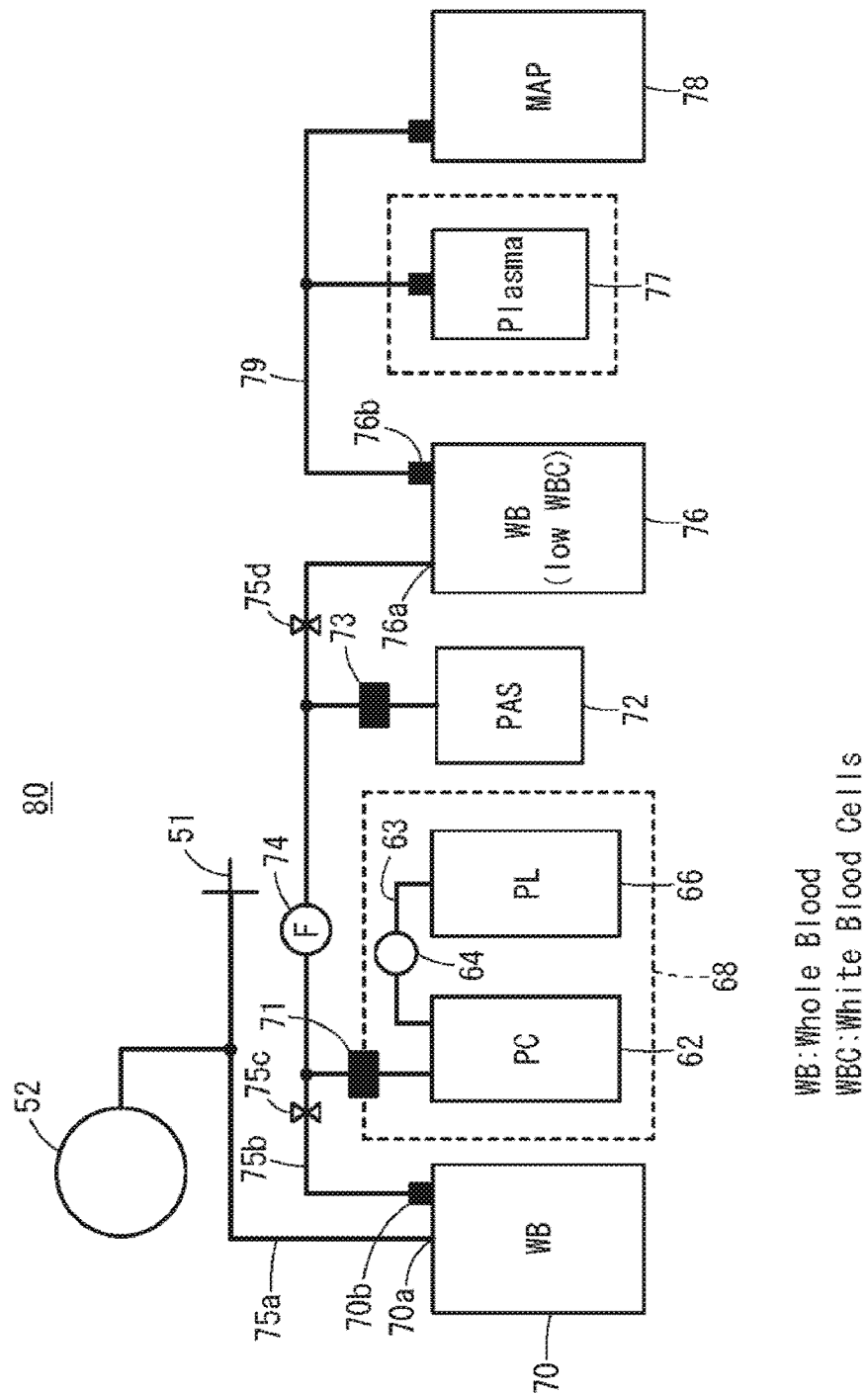
FIG. 16 is a block diagram illustrating a bag set according to a fourth embodiment.

In a case where the bag set 50 has no leukapheresis chamber 56 attached thereto, the platelet concentrate PC can be collected in the concentration bag set 68 by adding a step in which, as illustrated in FIG. 16, the buffy coat BC that contains platelet and leukocyte is obtained in apheresis (step S202), and the buffy coat BC is then centrifuged to remove the leukocyte.

Alternatively, the leukocyte may be removed by allowing the whole blood WB obtained from the donor to pass through leukapheresis filter, prior to apheresis by centrifugation (step S202).

The method for producing a platelet lysate of this embodiment demonstrates the following effects.

In the method for producing a platelet lysate includes, the step of collecting the platelet-containing component includes a step of centrifuging the whole blood WB from the donor to collect the platelet concentrate PC, and returning other components to the donor; a step of freezing and thawing the platelet concentrate PC; and the step of centrifuging, following freezing and thawing, the platelet concentrate PC to recover the platelet lysate PL. Since only the platelet can be collected from the donor, and the other components can be returned to the donor, so that the donor will be less stressed. Moreover, since the process is simplified and fewer bags will suffice, also the amount of waste can be reduced.

In the aforementioned method for producing a platelet lysate, leukocyte may be removed in the leukapheresis chamber 56, when the whole blood WB of the donor is centrifuged. An additional step of removing leukocyte will therefore be no longer necessary, and the structure of the bag set 50 can be simplified.

Fourth Embodiment

A bag set 80 of this embodiment illustrated in FIG. 16 is devised, when used for collecting the whole blood WB, so that the platelet can be recovered from the leukapheresis filter 74 which will be discarded after use.

The bag set 80 includes a blood collection unit 51 equipped with a puncture needle, an initial flow blood bag 52 that pools the initial flow blood, a first whole blood bag 70 that pools the whole blood WB coming from the blood collection unit 51, a second whole blood bag 76 connected to the downstream side of the first whole blood bag 70, a leukapheresis filter 74 connected between the first whole blood bag 70 and the second whole blood bag 76, and a preservation liquid bag 78 and a plasma recovery bag 77 that are connected to the second whole blood bag 76. The bag set 80 further includes a recovery liquid bag 72 connected to the downstream side of the leukapheresis filter 74, and the concentration bag set 68 connected to the upstream side of the leukapheresis filter 74.

The first whole blood bag 70 is made of a flexible resin film or the like, and has a first port 70a and a second port 70b. To the first port 70a of the first whole blood bag 70, there are connected the blood collection unit 51 and the initial flow blood bag 52, through a tube 75a. Meanwhile, to the second port 70b of the first whole blood bag 70 is connected a tube 75b through which the second whole blood bag 76 is connected. The second port 70b is made closable. The tube 75b has, connected therein, the leukapheresis filter 74.

The leukapheresis filter 74 is typically composed of a microfiber nonwoven fabric made of polyester-based ultrafine fiber, so as to remove leukocyte in the whole blood. The tube 75b between the leukapheresis filter 74 and the first whole blood bag 70 is provided with a first valve unit 75c, and the tube 75b between the leukapheresis filter 74 and the second whole blood bag 76 is provided with a second valve unit 75d. To the tube 75b between the first valve unit 75c and the leukapheresis filter 74, the concentration bag set 68 is connected. A clamp 71 is provided between the concentration bag set 68 and the tube 75b. To the tube 75b between the second valve unit 75d and the leukapheresis filter 74, the recovery liquid bag 72 is connected. A clamp 73 is provided between the recovery liquid bag 72 and the tube 75b.

The second whole blood bag 76 has a first port 76a and a second port 76b. To the first port 76a of the second whole blood bag 76, the first whole blood bag 70 is connected through the tube 75b. To the second whole blood bag 76, the whole blood WB from which leukocyte has been removed is introduced through the first port 76a. The second whole blood bag 76 has the tube 79 connected to the second port 76b, and through the tube 79, the plasma recovery bag 77 and the preservation liquid bag 78 are connected.

The preservation liquid bag 78 pools the blood preservation liquid (MAP), so as to enable feeding of the preservation liquid to the whole blood WB in the second whole blood bag 76. The plasma recovery bag 77 is devised to recover the plasma produced when the whole blood WB in the second whole blood bag 76 is centrifuged.

Figure 18A:
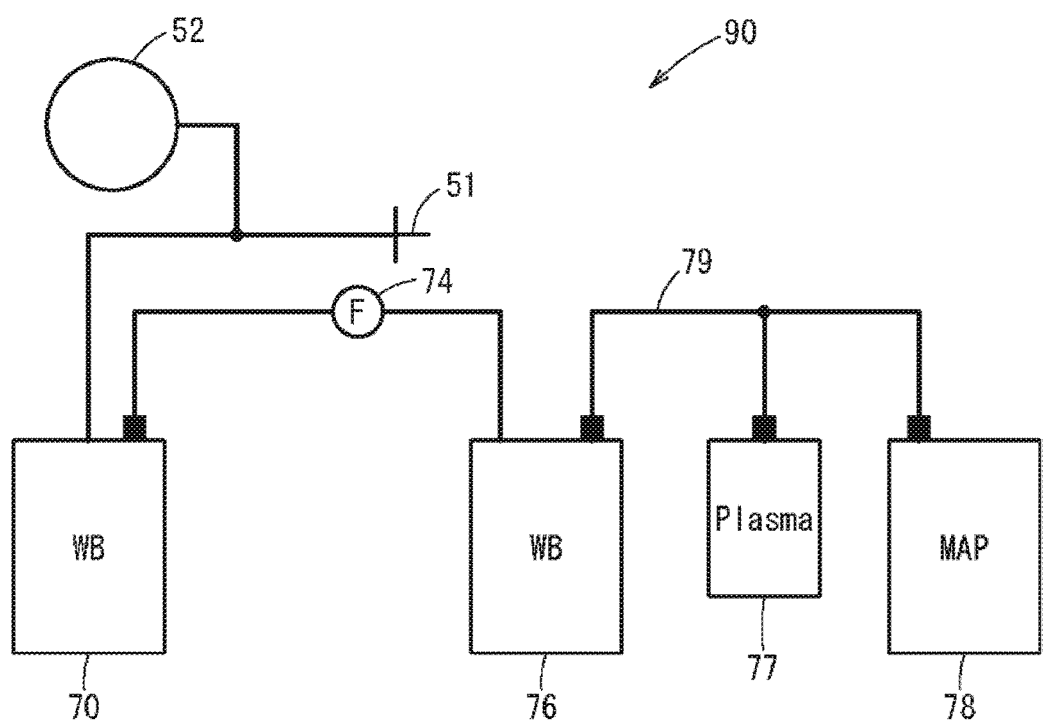
FIG. 18A is a block diagram illustrating a bag set according to a modified example of the fourth embodiment.
Figure 18B:
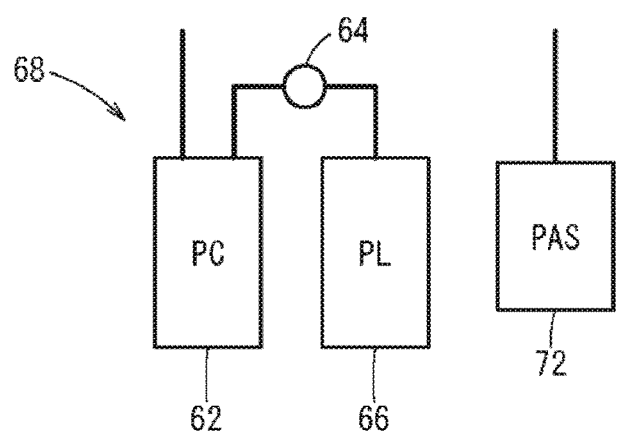
FIG. 18B is a block diagram illustrating a bag set for recovering platelet from a leukapheresis filter in FIG. 18A.

While the bag set 80 of this embodiment is constituted as described above, the concentration bag set 68, the recovery liquid bag 72, the plasma recovery bag 77, and the preservation liquid bag 78 are not always necessarily provided originally. For example, as illustrated in FIG. 18A, a bag set 90, from which the concentration bag set 68 and the recovery liquid bag 72 are omitted, is acceptable. In this case, the concentration bag set 68 and the recovery liquid bag 72 illustrated in FIG. 18B may be connected to the bag set 90 by using an aseptic joint, upon completion of removal of leukocyte from the whole blood WB.

Hereinafter, a method for producing a platelet lysate of this embodiment will be explained referring to FIG. 17.

First, the whole blood WB is collected from the donor (step S302). As illustrated in FIG. 16, step S302 is conducted so as to puncture the donor's blood vessel with the blood collection unit 51, to remove the initial flow blood with use of the initial flow blood bag 52, and to pool the whole blood WB in the first whole blood bag 70.

Figure 17:
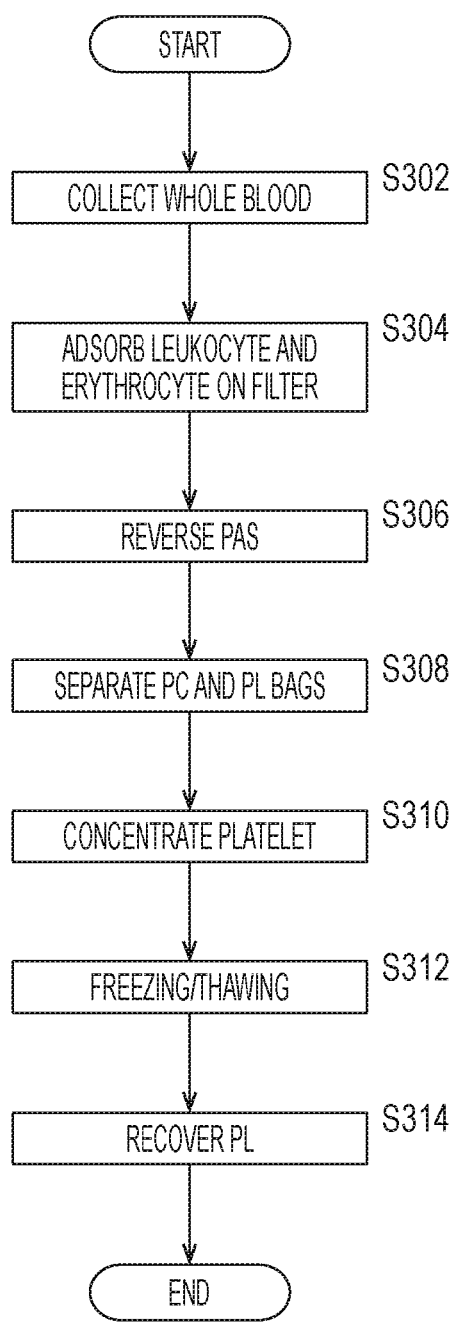
FIG. 17 is a flowchart illustrating a method for producing a platelet lysate according to a fourth embodiment.

Next, in step S304 in FIG. 17, leukocyte and platelet are captured (trapped) on the leukapheresis filter 74. That is, the whole blood WB in the first whole blood bag 70 in FIG. 16 is transferred through the second port 70b and the tube 75b, to the second whole blood bag 76. During the process, as the whole blood WB passes through the leukapheresis filter 74, leukocyte is captured and removed by the leukapheresis filter 74. Together with the leukocyte, also platelet is captured on the leukapheresis filter 74. The second whole blood bag 76 is then detached. The whole blood WB in the second whole blood bag 76 is used for various purposes such as a raw material for formulation or as blood for transfusion. The leukapheresis filter 74, having previously been discarded as it is, contains platelet which is effective as a cell culture medium as described above. Therefore, in this embodiment, platelet contained in the leukapheresis filter 74 is recovered and used.

That is, in step S306 in FIG. 17, the platelet recovery liquid is allowed to flow (flushed reversely) through the leukapheresis filter 74 from the side the whole blood WB flows out, towards the side the whole blood WB flows in. The platelet recovery liquid applicable here may be platelet additive solution (PAS), for example. In step S306, in the bag set 80 in FIG. 16, the first valve unit 75c and the second valve unit 75d are closed, and the clamp 71 and the clamp 73 are opened. This makes the recovery liquid bag 72 communicate with the downstream side of the leukapheresis filter 74, and makes the concentration bag set 68 communicate with the upstream side of the leukapheresis filter 74. The platelet recovery liquid in the recovery liquid bag 72 is then pressed out, so as to make the platelet recovery liquid flow (flushed reversely) through the leukapheresis filter 74 for rinsing. The platelet recovered from the leukapheresis filter 74 is recovered in the platelet recovery bag 62 of the concentration bag set 68, together with the platelet recovery liquid.

Figure 19:
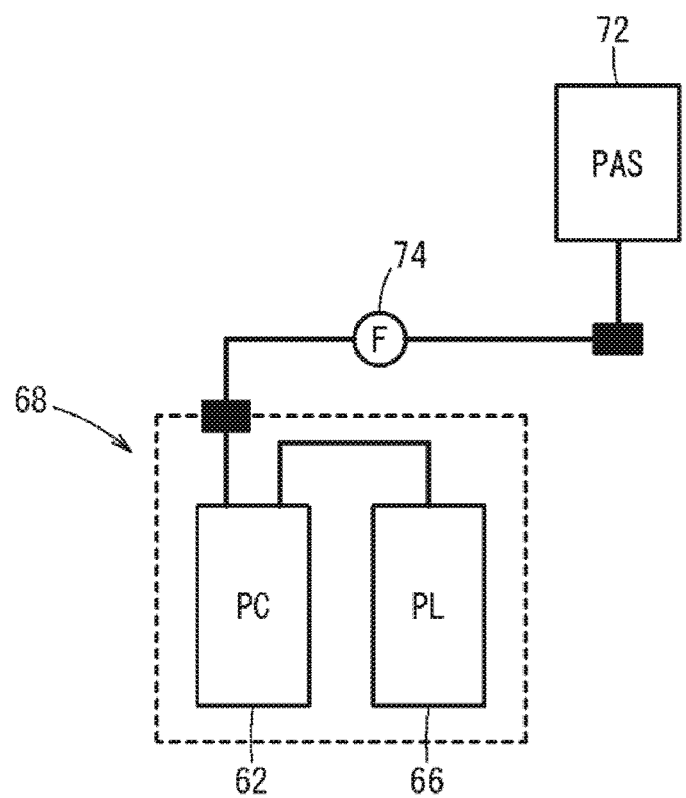
FIG. 19 is a block diagram illustrating a mode of connection of a bag set during recovery of platelet in the fourth embodiment.

Note that the operation in step S306 may be conducted, as illustrated in FIG. 19, with the leukapheresis filter 74 detached from the bag set 80. In this case, the recovery liquid bag 72 is connected to the outflow (downstream) side of the leukapheresis filter 74, and the concentration bag set 68 is connected to the upstream side of the leukapheresis filter 74. The platelet having been trapped on the leukapheresis filter 74 may be recovered, by flushing the platelet recovery liquid reversely from the downstream side of the leukapheresis filter 74.

Then in step S308 in FIG. 17, the concentration bag set 68 is separated. Next in step S310, the platelet is concentrated. That is, the concentration bag set 68 is set on the centrifuge 18 (see FIG. 1), and centrifuged. This causes sedimentation of a platelet-rich liquid, and the other components are separated as a supernatant. Upon removal of the supernatant from the platelet recovery bag 62, the platelet concentrate PC is obtained in the platelet recovery bag 62. Note that the centrifugation of the platelet-containing liquid is preferably conducted so as to concurrently remove leukocytes that are harmful to cell culture.

Next in step S312, the platelet concentrate PC in the concentration bag set 68 is frozen and thawed. Freezing and thawing in step S312 may be repeated a plurality of times. Platelet membrane is thus broken.

Next in step S314, the platelet lysate PL is recovered. That is, the concentration bag set 68 is set on the centrifuge 18, and the content of the platelet recovery bag 62 is centrifuged. The platelet lysate PL is thus obtained as a supernatant in the platelet recovery bag 62. The supernatant is recovered in the platelet lysate bag 66 to obtain the platelet lysate PL.

The method for producing a platelet lysate and the bag set 80 of this embodiment demonstrate the following effects.

The method for producing a platelet lysate according to this embodiment includes: a step (S302) of collecting whole blood WB from the donor; a step (S304) of allowing the collected whole blood WB to pass through the leukapheresis filter 74 to remove leukocyte; a step (S306) of flushing the platelet recovery liquid through the leukapheresis filter 74 through which the whole blood WB has been allowed to pass, in a direction opposite to a flow direction of the whole blood WB, to recover the platelet retained on the leukapheresis filter 74 as the platelet-containing liquid; a step (S310) of further centrifuging the platelet-containing liquid to remove a supernatant, and thus concentrating the platelet to prepare a platelet concentrate PC; a step (S312) of freezing and thawing the platelet concentrate PC; and a step (S314) of centrifuging the platelet concentrate PC, following freezing and thawing, to separate a supernatant which is recovered as the platelet lysate PL. This enables recovery for utilization of platelet from the leukapheresis filter 74 having been discarded after whole blood collection.

In the method for producing a platelet lysate, a step of removing leukocyte from the platelet-containing liquid may take place concurrently with the step (S310) of concentrating the platelet-containing liquid, or prior to the step (S310) of concentrating the platelet-containing liquid. This beneficially removes leukocyte that is harmful to cell culture.

The method for producing a platelet lysate may have a step of pooling the platelet-containing liquid collected from a plurality of donors, prior to the step (S310) of concentrating the platelet-containing liquid. That is, the platelet-containing liquid recovered from the plurality of leukapheresis filters 74 is pooled in the platelet recovery bag 62 in advance, and then centrifuged. This successfully reduces the number of runs of centrifugation, thereby beneficially improving the workability and productivity.

The bag set 80 of this embodiment includes the first whole blood bag 70; the leukapheresis filter 74 connected to the downstream side of the first whole blood bag 70; the second whole blood bag 76 connected through the leukapheresis filter 74 to the downstream side of the first whole blood bag 70; the recovery liquid bag 72 connected to the downstream side of the leukapheresis filter 74, and pools a platelet lift-off liquid (recovery liquid) for lifting off platelet from the leukapheresis filter 74; and the concentration bag set 68 connected to the upstream side of the leukapheresis filter 74. This enables recovery of platelet, having been adhered on the leukapheresis filter 74 for removing leukocyte from the whole blood WB, into the concentration bag set 68, with the aid of reverse flushing of the platelet lift-off liquid (recovery liquid).

In the bag set 80, the concentration bag set 68 may have the platelet recovery bag 62, and the platelet lysate bag 66 that is connected through the tube 63 to the platelet recovery bag 62.

Fifth Embodiment

Figure 20:
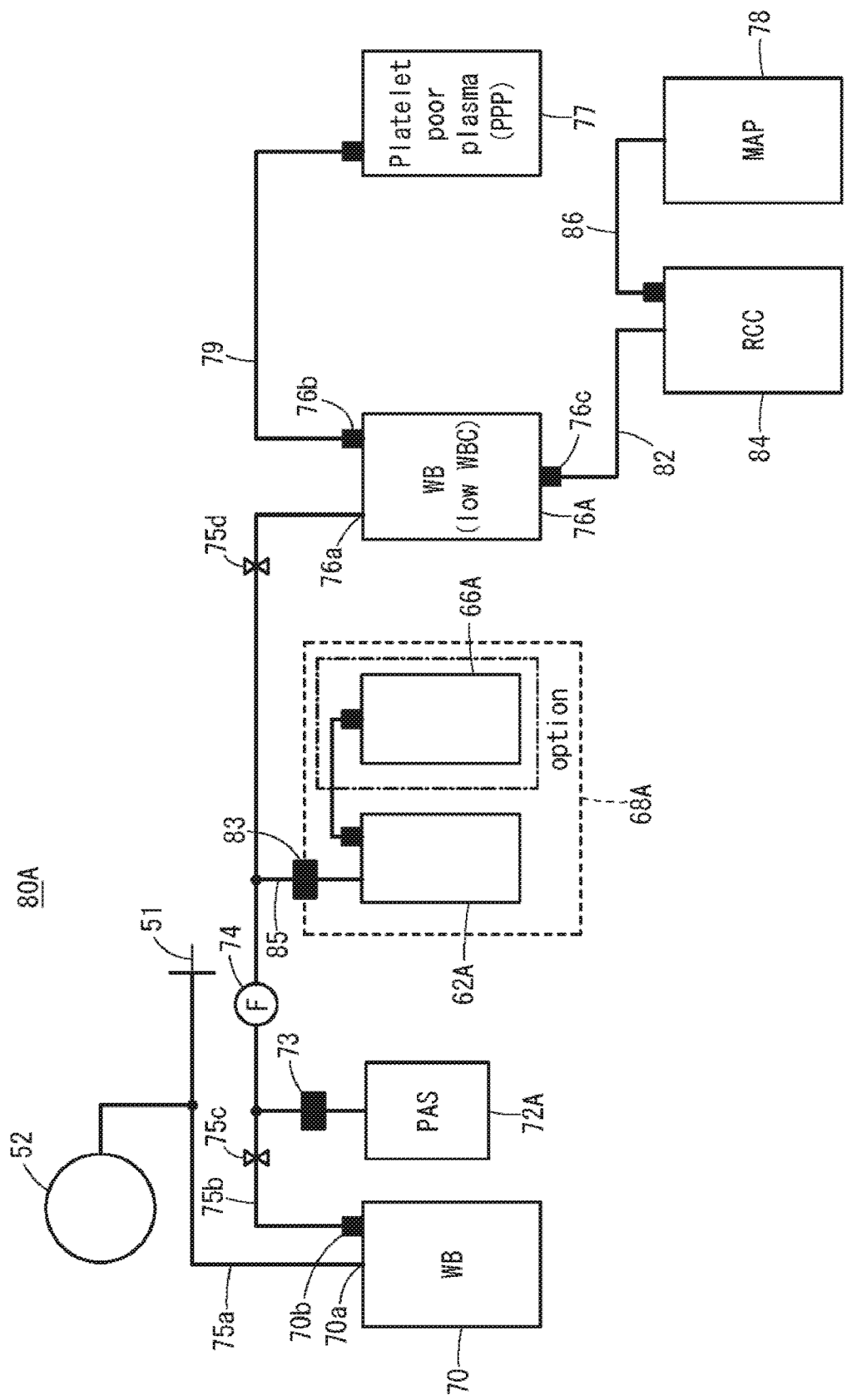
FIG. 20 is a block diagram illustrating a bag set according to a fifth embodiment.

A bag set 80A of this embodiment illustrated in FIG. 20 enables recovery of platelet, concurrently with collection of red cell concentrate (RCC) and platelet poor plasma (PPP) by centrifugation of the whole blood WB.

In the bag set 80A of this embodiment, all components similar to those of the bag set 80 in FIG. 16 are denoted by the same reference numerals, to skip the detailed explanation. As illustrated, the bag set 80A has a second whole blood bag 76A which is connected downstream of the first whole blood bag 70, through the leukapheresis filter 74A. The leukapheresis filter 74A is provided in the middle of the tube 75b that connects the first whole blood bag 70 and the second whole blood bag 76A. A recovery liquid bag 72A is connected to the tube 75b on the upstream side of the leukapheresis filter 74A, and a residual blood recovery bag 62A is connected to the tube 75b on the downstream side of the leukapheresis filter 74A.

The leukapheresis filter 74A is typically composed of a microfiber nonwoven fabric made of polyester-based ultrafine fiber, so as to remove white blood cell (WBC) in the whole blood, while allowing platelet to pass therethrough. The recovery liquid bag 72A is connected through the clamp 73 to the tube 75b. The recovery liquid bag 72A pools therein a rinsing liquid such as platelet additive solution (PAS).

The residual blood recovery bag 62A is connected to the tube 75b through a clamp 83. The residual blood recovery bag 62A is used to recover residual blood that remained on the leukapheresis filter 74A, after completion of transfer of the whole blood to the second whole blood bag 76A. The residual blood recovery bag 62A is given as a bag made of a flexible resin adaptable to centrifugation. The residual blood recovery bag 62A may have connected thereto a separation bag 66A, aiming at facilitating separation and recovery of a platelet-containing component obtained by centrifugation. The recovery bag set 68A in this case is composed of the residual blood recovery bag 62A and the separation bag 66A.

The second whole blood bag 76A is a top-and-bottom bag that has the ports (outlet ports) provided on the upper and lower sides thereof, with the first port 76a and the second port 76b arranged on the upper side, and with a third port 76c arranged on the lower side, as in the illustrated example. To the upper first port 76a, the tube 75b is connected. To the second port 76b, the plasma recovery bag 77 is connected through the tube 79. The plasma recovery bag 77 pools the platelet poor plasma (PPP) centrifuged in the second whole blood bag 76A. The second port 76b is provided with an easily tearable part which is kept closed until just before transfer of the platelet poor plasma.

To the third port 76c of the second whole blood bag 76A, an erythrocyte bag 84 is connected through a tube 82. The erythrocyte bag 84 pools the concentrated erythrocyte centrifuged in the second whole blood bag 76A. The third port 76c is provided with an easily tearable part which is kept closed until just before transfer of the concentrated erythrocyte. To the erythrocyte bag 84, the preservation liquid bag 78 is connected through a tube 86.

The preservation liquid bag 78 has enclosed therein an erythrocyte preservation liquid such as MAP solution. The tube 86 that connects the preservation liquid bag 78 and the erythrocyte bag 84 has, at the end thereof, an easily tearable part which is torn and opened just before use.

Figure 21:
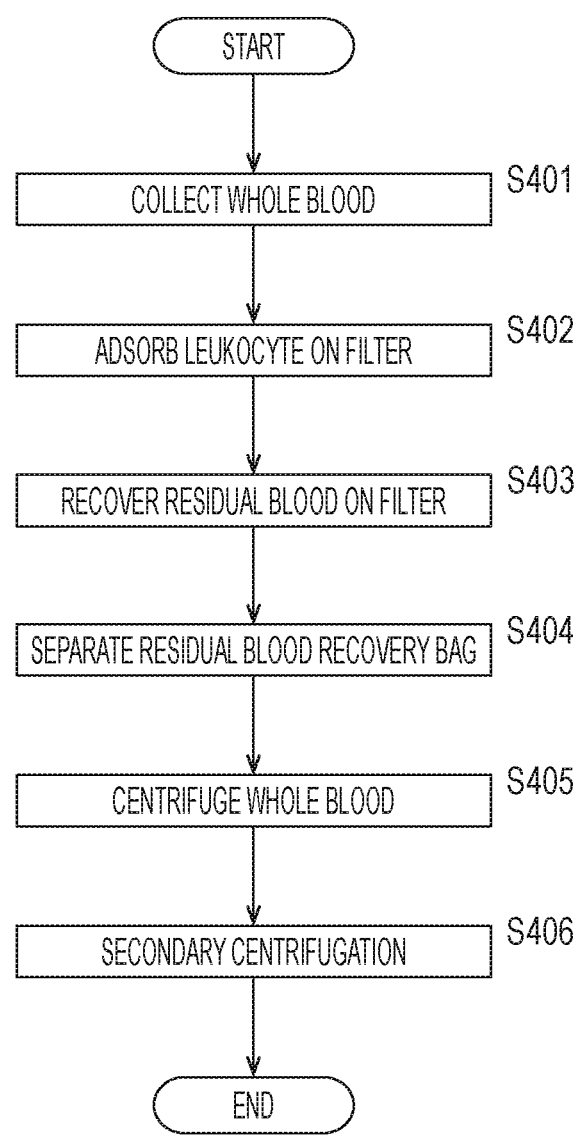
FIG. 21 is a flowchart illustrating a method for producing a platelet lysate according to the fifth embodiment.

Hereinafter, the method for producing a platelet lysate of this embodiment will be explained referring to FIGS. 21 and 22.

First, the whole blood WB is collected from the donor (step S401). The whole blood WB of the donor is pooled in the first whole blood bag 70.

Next, the whole blood WB in the first whole blood bag 70 is transferred through the tube 75b to the second whole blood bag 76A. During the process, leukocyte in the whole blood is removed by the leukapheresis filter 74A (step S402). Upon completion of transfer of the whole blood to the second whole blood bag 76A, the second valve unit 75d is closed.

Next, the residual blood on the leukapheresis filter 74A is recovered (step S403). The residual blood is recovered by closing the first valve unit 75c and the second valve unit 75d in FIG. 22, opening the clamps 73 and 83, and flushing the platelet additive solution PAS (rinsing liquid) in the recovery liquid bag 72A towards the residual blood recovery bag 62A. The leukapheresis filter 74A is rinsed with the platelet additive solution PAS, and the rinsate is pooled in the residual blood recovery bag 62A.

Figure 22:
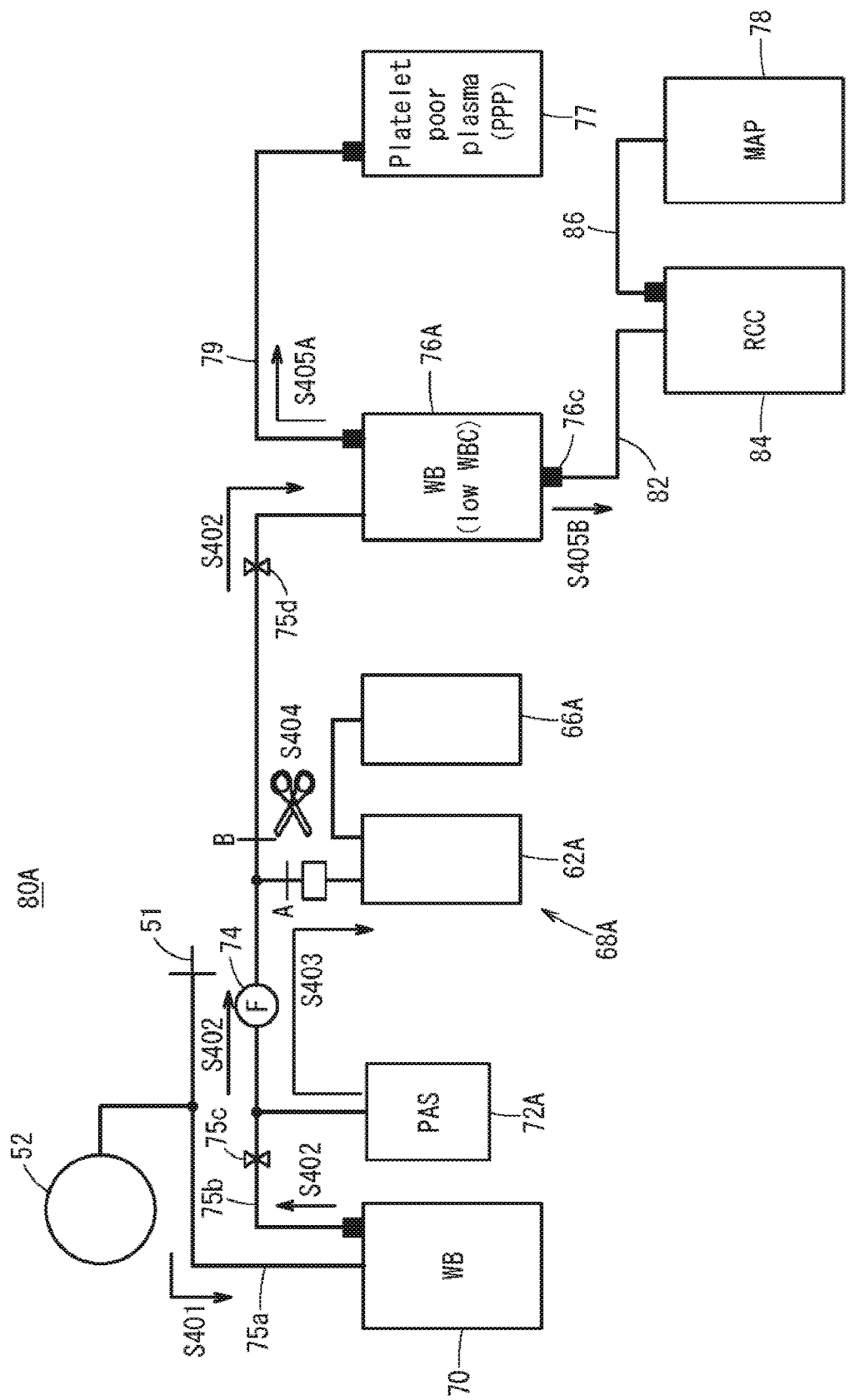
FIG. 22 is an explanatory drawing illustrating flow of liquid in a bag set, in the method for producing a platelet lysate according to the fifth embodiment.

Thereafter, the residual blood recovery bag 62A is separated from the tube 75b, at point A in FIG. 22 (step S404). The separation from the tube 75b is aseptically conducted by using an aseptic cutting device, by which the end is cut and heat-welded at the same time. In step S404, also the tube 75b is cut on the downstream side of the leukapheresis filter 74 (at point B in FIG. 22), thereby separating the second whole blood bag 76A.

Next, the second whole blood bag 76A, the plasma recovery bag 77, the erythrocyte bag 84, and the preservation liquid bag 78 are set on the centrifuge 18 (see FIG. 1), and the whole blood in the second whole blood bag 76A is centrifuged (step S405). By the centrifugation, the whole blood in the second whole blood bag 76A is separated into platelet-poor plasma (PPP), platelet-rich plasma (PRP), and red cell concentrate (RCC) when viewed from the upper layer side. The platelet-poor plasma (PPP) is then transferred to the plasma recovery bag 77, and the red cell concentrate (RCC) is transferred to the erythrocyte bag 84. In the second whole blood bag 76A, the platelet-rich plasma (PRP) remains.

Next, for the purpose of concentrating the platelet-rich plasma (PRP) that remains in the second whole blood bag 76A to obtain the platelet concentrate (PC), the second whole blood bag 76A is then subjected to secondary centrifugation (step S406).

Thereafter, the platelet lysate is produced according to the processes having been explained referring to steps S80 to S170 in FIG. 5.

Also the residual blood recovery bag 62A in FIG. 22 is centrifuged, thereby separating the buffy coat BC from the residual blood. The buffy coat BC separated in the residual blood recovery bag 62A is pooled, and the platelet lysate is produced according to the processes having been explained referring to steps S40 to S170 in FIG. 5.

As described above, in this embodiment, platelet is allowed to pass through the leukapheresis filter 74A (only leukocyte is removed), and the thus filtered whole blood is centrifuged to be separated into three layers, which are the platelet-poor plasma PPP, the platelet-rich plasma PRP, and concentrated erythrocyte RCC. Then, the platelet-rich plasma (PRP), which is a middle layer component remained in the second whole blood bag 76A, is processed to obtain the platelet concentrate (PC). In addition, the blood (whole blood) remaining on the leukapheresis filter 74 is rinsed (washed) with the platelet additive solution PAS, and the rinsate is recovered and centrifuged in the residual blood recovery bag 62A. This enables recovery of platelet without waste both from the whole blood having been passed through the leukapheresis filter 74A, and from the blood that remains on the leukapheresis filter 74A.

Having been explained the present invention referring to preferred embodiments, the present invention is not limited to the aforementioned embodiments, and may of course be modified in various ways without departing from the spirit of the present invention.

The invention claimed is:

1. A bag set for recovering platelet from a leukapheresis filter, the bag set comprising:
   a first whole blood bag that pools whole blood of a donor;
   a leukapheresis filter connected to a downstream side of the first whole blood bag;
   a second whole blood bag connected through the leukapheresis filter to the downstream side of the first whole blood bag;
   a recovery liquid bag connected to a downstream side of the leukapheresis filter, and pooling a platelet recovery liquid for recovering platelet from the leukapheresis filter;
   a concentration bag set connected to an upstream side of the leukapheresis filter, wherein the concentration bag set includes a platelet recovery bag and a platelet lysate bag connected through a tube and a filter to the platelet recovery bag; and
   a first tube that connects the first whole blood bag to the second whole blood bag through the leukapheresis filter, wherein the first tube includes:
   a first branch that connects to the platelet recovery bag; and
   a second branch that connects to the recovery liquid bag.

2. The bag set according to claim 1, further comprising:
   a valve positioned in the first tube between the first whole blood bag and the first branch of the first tube.

3. A bag set for recovering platelet from a leukapheresis filter, the bag set comprising:
   a first whole blood bag that pools whole blood of a donor;
   a leukapheresis filter connected to a downstream side of the first whole blood bag;
   a second whole blood bag connected through the leukapheresis filter to the downstream side of the first whole blood bag;
   a recovery liquid bag connected to an upstream side of the leukapheresis filter, and pooling a rinsing liquid for recovering residual blood from the leukapheresis filter;
   a residual blood recovery bag connected to a downstream side of the leukapheresis filter;
   a recovery bag set connected to the downstream side of the leukapheresis filter through a clamp, wherein the recovery bag set includes the residual blood recovery bag and a separation bag connected through a first tube to the residual blood recovery bag; and
   a second tube that connects the first whole blood bag to the second whole blood bag through the leukapheresis filter, wherein the second tube includes:
   a first branch that connects to the recovery liquid bag; and a second branch that connects to the residual blood recovery bag.

* * * * *